(12) United States Patent
Dropinski et al.

(10) Patent No.: US 7,629,372 B2
(45) Date of Patent: Dec. 8, 2009

(54) COMPOUNDS FOR THE TREATMENT OF DYSLIPIDEMIA AND OTHER LIPID DISORDERS

(75) Inventors: James F. Dropinski, Colts Neck, NJ (US); Guo Q. Shi, Monmouth Junction, NJ (US); Yong Zhang, West Windsor, NJ (US)

(73) Assignee: Merck & Co., Inc., Rahway, NJ (US)

( * ) Notice: Subject to any disclaimer, the term of this patent is extended or adjusted under 35 U.S.C. 154(b) by 483 days.

(21) Appl. No.: 11/662,808

(22) PCT Filed: Sep. 12, 2005

(86) PCT No.: PCT/US2005/032557

§ 371 (c)(1),
(2), (4) Date: Mar. 13, 2007

(87) PCT Pub. No.: WO2006/033891

PCT Pub. Date: Mar. 30, 2006

(65) Prior Publication Data

US 2008/0039514 A1  Feb. 14, 2008

Related U.S. Application Data

(60) Provisional application No. 60/610,466, filed on Sep. 16, 2004.

(51) Int. Cl.
*A61K 31/423* (2006.01)
*C07D 261/20* (2006.01)

(52) U.S. Cl. ............... 514/379; 548/240; 548/241; 514/378

(58) Field of Classification Search .............. 548/240, 548/241; 514/378, 379
See application file for complete search history.

(56) References Cited

U.S. PATENT DOCUMENTS 6,569,879 B2   5/2003   Liu et al.
6,713,508 B2   3/2004   Sahoo et al.

FOREIGN PATENT DOCUMENTS

WO   WO 97/28137       8/1997
WO   WO 2004/011448    2/2004

*Primary Examiner*—Golam M Shameem
(74) *Attorney, Agent, or Firm*—Mark R. Daniel; James McGinnis

(57) ABSTRACT

A class of compounds having Formula I and pharmaceutically acceptable salts thereof are useful as therapeutic compounds, particularly in the treatment of hyperlipidemia, hypercholesterolemia, dyslipidemia, and other lipid disorders, and in delaying the onset of or reducing the risk of developing conditions and sequelae that are associated with these diseases, such as atherosclerosis.

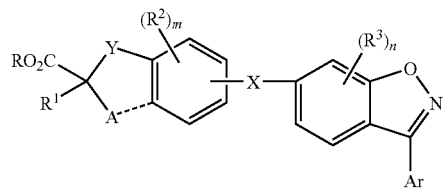

12 Claims, No Drawings

COMPOUNDS FOR THE TREATMENT OF DYSLIPIDEMIA AND OTHER LIPID DISORDERS

CROSS REFERENCE TO RELATED APPLICATIONS

This application is a U.S. National Phase application under 35 U.S.C. § 371 of PCT Application No. PCT/US2005/032557, filed Sep. 12, 2005, which claims priority under 35 U.S.C. § 119(e) from U.S. Application No. 60/610,466, filed Sep. 16, 2004.

FIELD OF THE INVENTION

The instant invention is concerned with a class of benzisoxazole compounds and pharmaceutically acceptable salts thereof which are useful as therapeutic compounds, particularly in the treatment and control of hyperlipidemia, hypercholesterolemia, dyslipidemia, and other lipid disorders, and in delaying the onset of or reducing the risk of conditions and sequelae that are associated with these diseases, including atherosclerosis and Type 2 diabetes mellitus, often referred to as non-insulin dependent diabetes (NIDDM).

BACKGROUND OF THE INVENTION

Disorders of lipid metabolism (dyslipidemias) include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as Low Density Lipoproteins (LDL), Very Low Density Lipoproteins (VLDL) and Intermediate Density Lipoproteins (IDL)). Cholesterol is mostly carried in Low Density Lipoproteins (LDL), and this component is commonly known as the "bad" cholesterol because it has been shown that elevations in LDL-cholesterol correlate closely to the risk of coronary heart disease. A smaller component of cholesterol is carried in the High Density Lipoproteins (HDL) and is commonly known as the "good" cholesterol. In fact, it is known that the primary function of HDL is to accept cholesterol deposited in the arterial wall and to transport it back to the liver for disposal through the intestine. Although it is desirable to lower elevated levels of LDL cholesterol, it is also desirable to increase levels of HDL cholesterol. Generally, it has been found that increased levels of HDL are associated with a lower risk for coronary heart disease (CHD). See, for example, Gordon, et al., Am. J. Med., 62, 707-714 (1977); Stampfer, et al., N. England J. Med., 325, 373-381 (1991); and Kannel, et al., Ann. Internal Med., 90, 85-91 (1979). An example of an HDL raising agent is nicotinic acid, a drug with limited utility because doses that achieve HDL raising are associated with undesirable effects, such as flushing.

Dyslipidemias were originally classified by Fredrickson according to the combination of alterations mentioned above. The Fredrickson classification includes 6 phenotypes (i.e., I, IIa, IIb, III, IV and V) with the most common being the isolated hypercholesterolemia (or type IIa) which is usually accompained by elevated concentrations of total and LDL cholesterol. The initial treatment for hypercholesterolemia is often to modify the diet to one low in fat and cholesterol, coupled with appropriate physical exercise, followed by drug therapy when LDL-lowering goals are not met by diet and exercise alone.

A second common form of dyslipidemia is the mixed or combined hyperlipidemia or type IIb and III of the Fredrickson classification. This dyslipidemia is often prevalent in patients with type 2 diabetes, obesity and the metabolic syndrome. In this dyslipidemia there are modest elevations of LDL-cholesterol, accompanied by more pronounced elevations of small dense LDL-cholesterol particles, VLDL and/or IDL (i.e., triglyceride rich lipoproteins), and total triglycerides. In addition, concentrations of HDL are often low.

Peroxisome proliferators are a structurally diverse group of compounds that when administered to rodents elicit dramatic increases in the size and number of hepatic and renal peroxisomes, as well as concomitant increases in the capacity of peroxisomes to metabolize fatty acids via increased expression of the enzymes of the beta-oxidation cycle. Compounds of this group include but are not limited to the fibrate class of lipid modulating drugs, herbicides, phthalate plasticizers and the glitazones, a class of compounds that has been under investigation for the treatment of type 2 diabetes. Peroxisome proliferation is also triggered by dietary or physiological factors such as a high-fat diet and cold acclimatization.

Three sub-types of peroxisome proliferator activated receptor (PPAR) have been discovered and described; they are peroxisome proliferator activated receptor alpha (PPARα), peroxisome proliferator activated receptor gamma (PPARγ) and peroxisome proliferator activated receptor delta (PPARδ). PPARα is activated by a number of medium and long-chain fatty acids, and it is involved in stimulating β-oxidation of fatty acids. PPARα is also associated with the activity of fibrates and fatty acids in rodents and humans. Fibric acid derivatives such as clofibrate, fenofibrate, bezafibrate, ciprofibrate, beclofibrate and etofibrate, as well as gemfibrozil, each of which are PPARα ligands and/or activators, produce a substantial reduction in plasma triglycerides as well as some increase in HDL. The effects on LDL cholesterol are inconsistent and might depend upon the compound and/or the dyslipidemic phenotype. For these reasons, this class of compounds has been primarily used to treat hypertriglyceridemia (i.e, Fredrickson Type IV and V) and/or mixed hyperlipidemia.

The PPARγ receptor subtypes are involved in activating the program of adipocyte differentiation and are not involved in stimulating peroxisome proliferation in the liver. There are two known protein isoforms of PPARγ: PPARγ1 and PPARγ2 which differ only in that PPARγ2 contains an additional 28 amino acids present at the amino terminus. The DNA sequences for the human isotypes are described in Elbrecht, et al., BBRC 224;431-437 (1996). In mice, PPARγ2 is expressed specifically in fat cells. Tontonoz et al., Cell 79: 1147-1156 (1994) provide evidence to show that one physiological role of PPARγ2 is to induce adipocyte differentiation. As with other members of the nuclear hormone receptor superfamily, PPARγ2 regulates the expression of genes through interaction with other proteins and binding to hormone response elements, for example in the 5' flanking regions of responsive genes. An example of a PPARγ2 responsive gene is the tissue-specific adipocyte P2 gene. Although peroxisome proliferators, including the fibrates and fatty acids, activate the transcriptional activity of PPAR's, only prostaglandin $J_2$ derivatives have been identified as potential natural ligands of the PPARγ subtype, which also binds thiazolidinedione antidiabetic agents with high affinity.

The human nuclear receptor gene PPARδ (hPPARδ) has been cloned from a human osteosarcoma cell cDNA library and is fully described in A. Schmidt et al., Molecular Endocrinology, 6:1634-1641 (1992). It should be noted that PPARδ is also referred to in the literature as PPARβ and as NUC1, and each of these names refers to the same receptor; in Schmidt et al. the receptor is referred to as NUC1.

In WO96/01430, a human PPAR subtype, hNUC1B, is disclosed. The amino acid sequence of hNUC1B differs from human PPARδ (referred to therein as hNUC1) by one amino acid, i.e., alanine at position 292. Based on in vivo experiments described therein, the authors suggest that hNUC1B protein represses hPPARα and thyroid hormone receptor protein activity.

It has been disclosed in WO97/28149 that agonists of PPARδ are useful in raising HDL plasma levels. PPARδ agonists have recently been disclosed in WO 2002/100351 as having utility in the treatment of various inflammatory diseases, such as rheumatoid arthritis. WO97/27857, 97/28115, 97/28137 and 97/27847 disclose compounds that are useful as antidiabetic, antiobesity, anti-atherosclerosis and antihyperlipidemic agents, and which activate PPARs.

It is generally believed that glitazones exert their effects by binding to the peroxisome proliferator activated receptor (PPAR) family of receptors, controlling certain transcription elements having to do with the biological entities listed above. Glitazones are benzyl-2,4-thiazolidinedione derivatives. See Hulin et al., Current Pharm. Design (1996) 2, 85-102.

A number of glitazones that are PPAR agonists have been approved for use in the treatment of diabetes. These include troglitazone, rosiglitazone and pioglitazone, all of which are primarily or exclusively PPARγ agonists. Many of the newer PPAR agonists that are currently under development or are in clinical trials do not have a glitazone structure and have dual PPARα and γ activity, such as muraglitazar, naveglitazar (LY-818), TAK-559, and tesaglitazar. The PPARα/γ agonists are expected to improve both insulin sensitivity and the lipid profile in patients having NIDDM.

Compounds that are agonists of the various PPAR subtypes are expected to be useful in the treatment of diseases and conditions that respond to treatment with PPAR agonists. These include dyslipidemia, diabetes, and related conditions. PPARα agonists improve the lipid profile and alleviate dyslipidemias by reducing elevated LDL levels, reducing elevated triglyceride levels, and increasing HDL levels. PPARγ agonists improve insulin sensitivity, reducing the need for insulin secretagogues and insulin injections in patients with NIDDM. The role of PPARδ is less well defined, but PPARδ also appears to help control hyperlipidemia and hyperglycemia in type 2 diabetic patients.

SUMMARY OF THE INVENTION

The class of compounds described herein is a new class of potent and selective PPAR agonists. The compounds generally exhibit high activity at the PPARα receptor. Many of the compounds exhibit little or no activity at the PPARγ and PPARδ receptors, as evidenced by their assay data, so that they are selective for PPARα. The compounds are useful in the treatment of diseases, disorders and conditions that are treated or ameliorated by PPARα agonists.

The compounds are useful in treating one or more of the following conditions: mixed or diabetic dyslipidemia; other lipid disorders, including isolated hypercholesterolemia as manifested by elevations in LDL-C and/or non-HDL-C; hyperapoBliproteinemia; hypertriglyceridemia; elevated triglyceride-rich-lipoproteins; and low HDL cholesterol concentrations. The compounds also have utility in the treatment of atherosclerosis, obesity, and vascular restenosis. They may also be useful in treating inflammatory conditions and insulin sensitivity. As a result of their utility in treating and ameliorating one or more of lipid disorders, obesity, dyslipidemia, and insulin sensitivity, the compounds also may be effective in treating or ameliorating the metabolic syndrome, also known as Syndrome X, thereby reducing the risk of developing atherosclerosis.

The present invention provides compounds having the structure of Formula I, including pharmaceutically acceptable salts and prodrugs of these compounds:

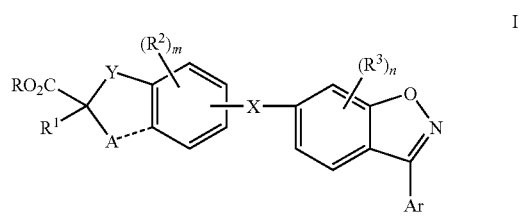

In the compounds having Formula I:

X and Y are each independently O or S;

A is selected from the group consisting of H, —$C_1$-$C_3$ alkyl which is optionally substituted with 1-5 halogens, —$CR^4R^5$—, and —$CR^4R^5O$—, wherein when A is —$CR^4R^5$— or —$CR^4R^5O$—, the dotted line between A and the phenyl ring of Formula I represents a single bond, and when A is —$CR^4R^5O$—, the O of —$CR^4R^5O$— is connected to the phenyl ring, and when A is H or —$C_1$-$C_3$ alkyl, the dotted line does not represent a bond;

R is H or $C_{1-6}$ alkyl, which is optionally substituted with 1-5 halogens;

$R^1$ is selected from H, halogen, and $C_1$-$C_4$ alkyl, which is optionally substituted with 1-5 halogens;

$R^2$ and $R^3$ are independently selected from the group consisting of H, halogen, $C_2$-$C_4$alkenyl, and $C_1$-$C_4$alkyl, wherein $C_1$-$C_4$alkyl and C2-C4alkenyl are optionally substituted with 1-5 halogens;

$R^4$ and $R^5$ are each independently selected from H, halogen, and $C_1$-$C_3$ alkyl, wherein $C_1$-$C_3$ alkyl is optionally substituted with 1-5 halogens;

m is 0, 1, or 2;

n is 0, 1, or 2;

Ar is phenyl, which is optionally substituted with 1-3 substituent groups independently selected from halogen —$C_1$-$C_4$alkyl, —$OC_1$-$C_4$alkyl, and —$NR^6R^7$, wherein —$C_1$-$C_4$alkyl and —$OC_1$-$C_4$alkyl are optionally substituted with 1-5 halogens; and $R^6$ and $R^7$ are each independently H or $C_1$-$C_3$alkyl.

In the above summary, reference to alkyl groups by carbon number, such as —$C_3$ alkyl or —$C_3$-$C_6$ alkyl, refers to both linear and branched alkyl groups.

The compounds described above are effective in treating diseases or conditions that respond to treatment with PPARα agonists. The compounds are expected to be efficacious in treating and ameliorating one or more of the following diseases or conditions: hyperlipidemia, dyslipidemia, hypercholesterolemia, hypertrigyceridemia, hyperglycemia, and obesity. The compounds may also be efficacious in treating non-insulin dependent diabetes mellitus (NIDDM) and/or conditions that are often associated with NIDDM, but which may be present in non-diabetic patients as well, including hyperlipidemia, dyslipidemia, hypercholesterolemia, hypertrigyceridemia, and obesity. The compounds may also be effective in treating atherosclerosis, hyperinsulinemia, vascular restenosis, and inflammatory conditions. The compounds may be effective in delaying or reducing the risk of some of the sequelae of NIDDM, such as atherosclerosis, vascular restenosis, and retinopathy by ameliorating the conditions that contribute to the development of these diseases. They may also be effective in reducing cardiovascular events that occur in human patients having metabolic syndrome, such as coronary heart disease, by ameliorating some of the risk factors that are associated with metabolic syndrome.

DETAILED DESCRIPTION OF THE INVENTION

The invention has numerous embodiments. Several preferred sub-groups of compounds are described below:

In one embodiment of the invention, the compounds of Formula I are defined as follows, and include pharmaceutically acceptable salts:

X and Y are O and are meta or para to each other;

$R^1$ is selected from —$CH_3$, —$C_2H_5$, n-$C_3H_7$, and —CH($CH_3$)$_2$;

$R^2$ and $R^3$ are independently selected from halogen, —$C_1$-$C_3$alkyl, and —$C_2$-$C_3$alkenyl, wherein —$C_1$-$C_3$ alkyl and —$C_2$-$C_3$alkenyl are optionally substituted with 1-3 halogens;

m and n are each independently 0 or 1;

A is selected from the group consisting of H, —$CH_3$, —$CH_2$— and —$CH_2O$—, wherein when A is H or —$CH_3$, the dotted line does not represent a bond; and when A is —$CH_2$— or —$CH_2O$—, the dotted line between A and the phenyl ring of Figure I represents a single bond, and the O of —$CH_2O$— is connected to the phenyl ring;

Ar is phenyl which is optionally substituted with 1-2 groups which are independently selected from —$CF_3$, —$OCF_3$, $C_1$-$C_3$ alkyl, halogen, and —$NR^6R^7$; and $R^6$ and $R^7$ are independently selected from H and $C_1$-$C_3$ alkyl.

A sub-group of compounds of Formula I have Formula Ia, shown below, including pharmaceutically acceptable salts:

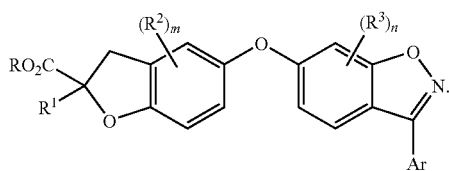

Ia

The substituent groups in Formula Ia have the definitions that were provided above.

In other embodiments, the substituent groups of Formula Ia, including pharmaceutically acceptable salts, have the following definitions:

$R^1$ is selected from —$CH_3$, —$C_2H_5$, n-$C_3H_7$, and —CH($CH_3$)$_2$;

$R^2$ and $R^3$ are independently selected from the group consisting of halogen, —$C_1$-$C_3$alkyl, and —$C_2$-$C_3$alkenyl, wherein —$C_1$-$C_3$alkyl, and —$C_2$-$C_3$alkenyl are optionally substituted with 1-3 halogens;

m and n are each independently 0 or 1;

Ar is phenyl which is optionally substituted with 1-2 groups which are independently selected from —$CF_3$, —$OCF_3$, —$C_1$-$C_3$ alkyl, halogen, and $NR^6R^7$; and $R^6$ and $R^7$ are independently selected from the group consisting of H and —$C_1$-$C_3$ alkyl.

A sub-group of compounds of Formula I has Formula Ib, shown below, including pharmaceutically acceptable salts:

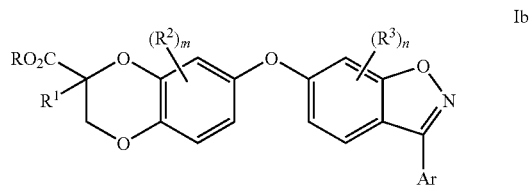

Ib

The substituent groups in Formula Ib have the definitions that were provided previously.

In other embodiments, the substituent groups of Formula Ib have the following definitions, including pharmaceutically acceptable salts:

$R^1$ is selected from —$CH_3$, —$C_2H_5$, n-$C_3H_7$, and —CH($CH_3$)$_2$;

$R^2$ and $R^3$ are independently selected from the group consisting of halogen, —$C_1$-$C_3$alkyl, and —$C_2$-$C_3$alkenyl, wherein —$C_1$-$C_3$alkyl, and —$C_2$-$C_3$alkenyl are optionally substituted with 1-3 halogens;

m and n are each independently 0 or 1;

Ar is phenyl which is optionally substituted with 1-2 groups which are independently selected from —$CF_3$, —$OCF_3$, —$C_1$-$C_3$ alkyl, halogen, and $NR^6R^7$; and $R^6$ and $R^7$ are independently selected from the group consisting of H and —$C_1$-$C_3$ alkyl.

A sub-group of compounds of Formula I have Formula Ic, shown below, including pharmaceutically acceptable salts:

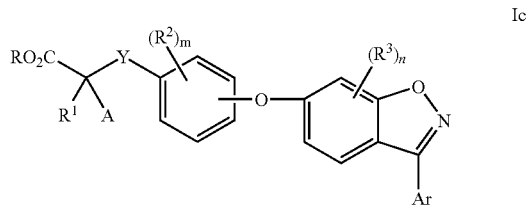

Ic

In the compounds of Formula Ic, the substituent groups have the following definitions:

Y is O and is meta or para to the O substituent on the phenyl ring to which Y is attached; and A is selected from the group consisting of H and —$C_1$-$C_3$ alkyl, which is optionally substituted with 1-5 halogens.

The other substituents are as defined previously.

In other embodiments, the substituent groups of Formula Ic have the following definitions, including pharmaceutically acceptable salts:

$R^1$ is selected from —$CH_3$, —$C_2H_5$, n-$C_3H_7$, and —CH($CH_3$)$_2$;

A is H or —$CH_3$;

$R^2$ and $R^3$ are independently selected from the group consisting of halogen, —$C_1$-$C_3$alkyl, and —$C_2$-$C_3$alkenyl, wherein —$C_1$-$C_3$alkyl, and —$C_2$-$C_3$alkenyl are optionally substituted with 1-3 halogens;

m and n are each independently 0 or 1;

Ar is phenyl which is optionally substituted with 1-2 groups which are independently selected from —$CF_3$, —$OCF_3$, —$C_1$-$C_3$ alkyl, halogen, and $NR^6R^7$; and $R^6$ and $R^7$ are independently selected from the group consisting of H and —$C_1$-$C_3$ alkyl.

In general, in the compounds of this invention, the preferred value of R is H.

In general, in the compounds of this invention, a preferred value of $R^1$ is $C_1$-$C_4$ alkyl.

Specific compounds are illustrated by the chemical structures shown in Table 1 below. The compounds are named in Table 2, immediately after Table 1. The specific compounds also include pharmaceutically acceptable salts.

TABLE 1

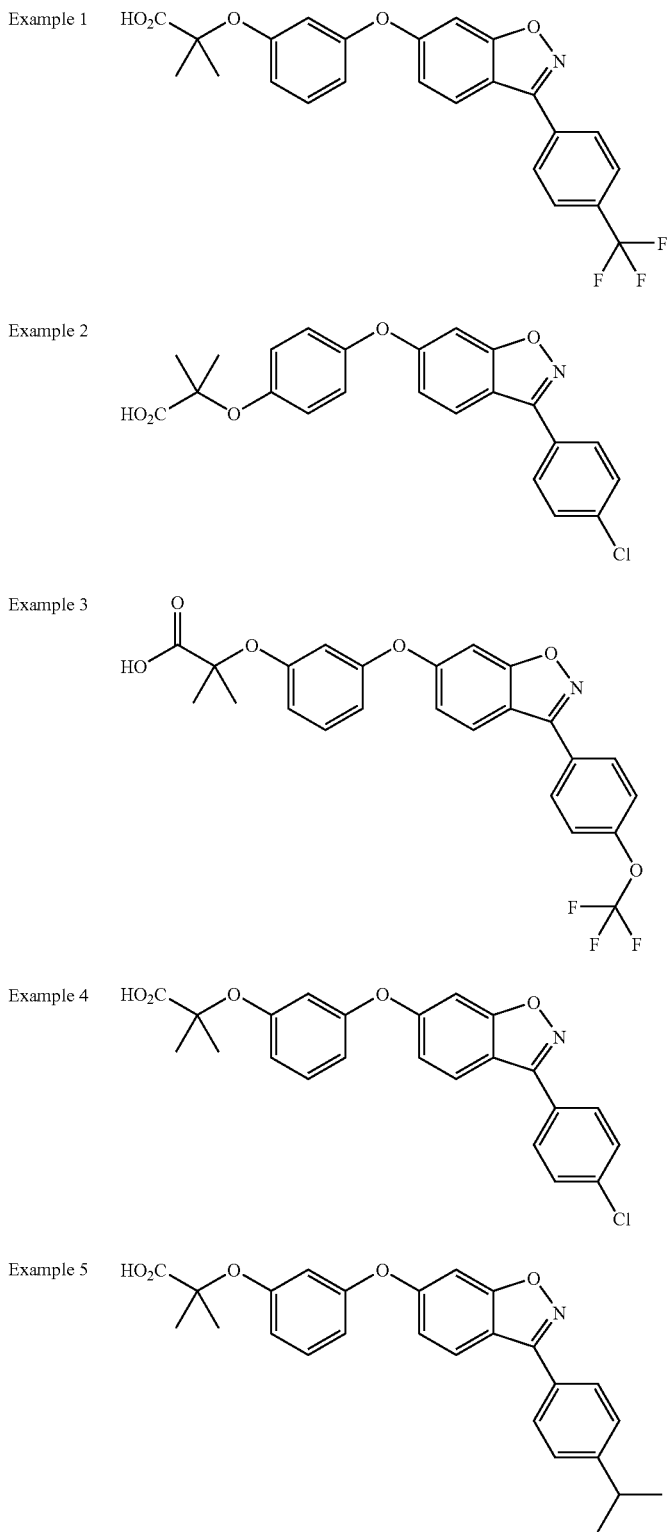

TABLE 1-continued
| Example 6 | 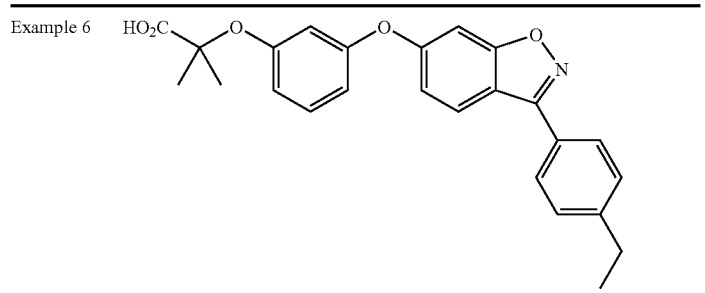 |
| --- | --- |
| Example 7 | 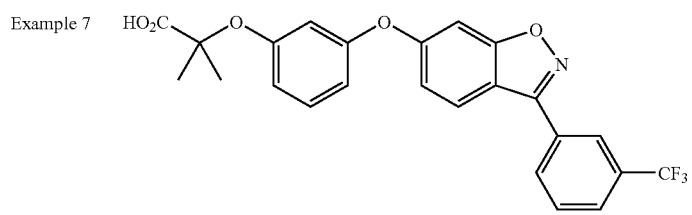 |
| Example 8 | 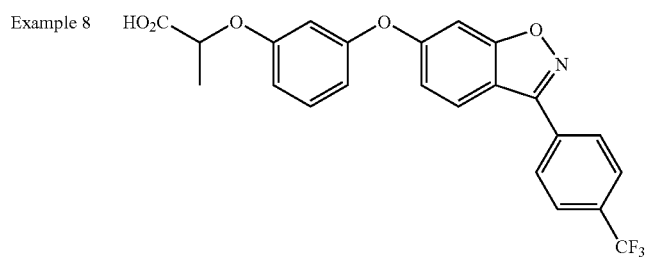 |
| Example 9 | 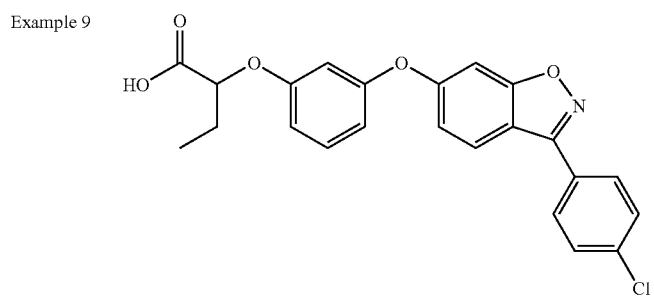 |
| Example 10 | 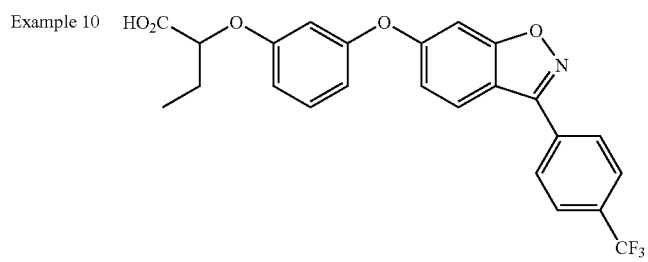 |
| Example 11 | 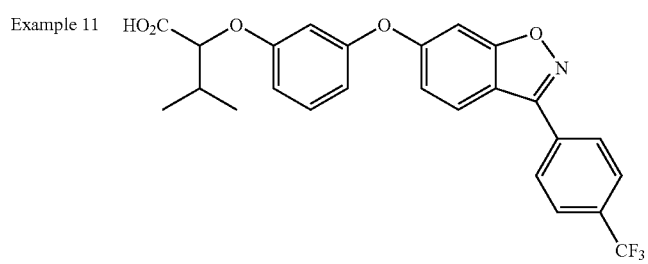 |

TABLE 1-continued
Example 12 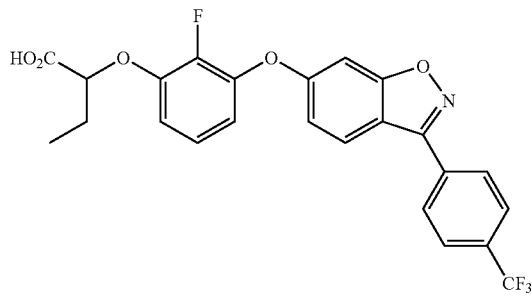
Example 13 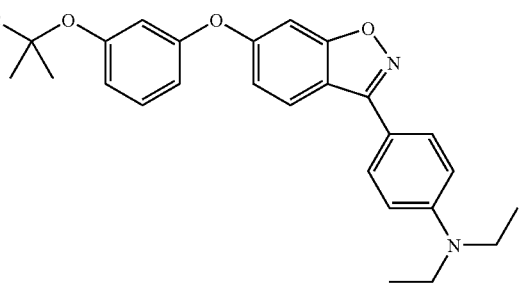
Example 14 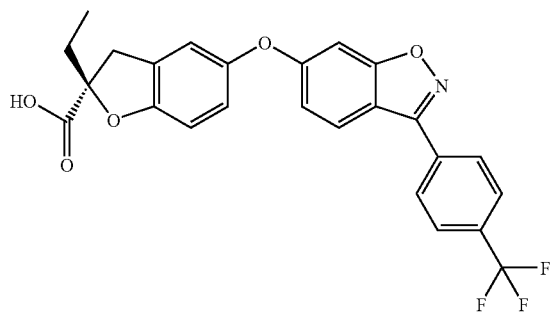
Example 15 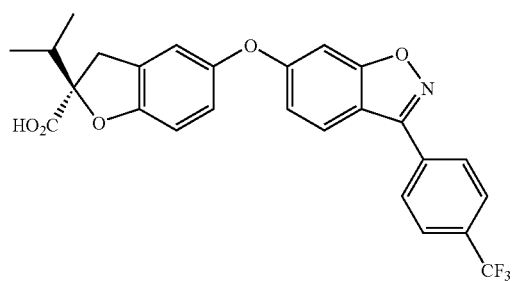
Example 16 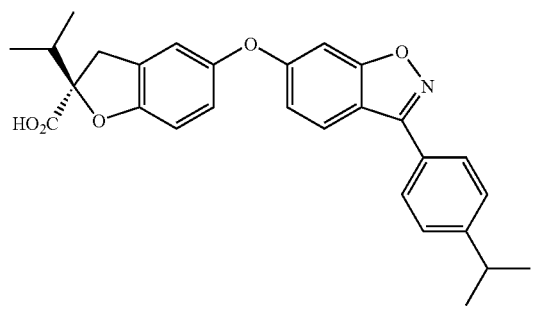

TABLE 1-continued
Example 17 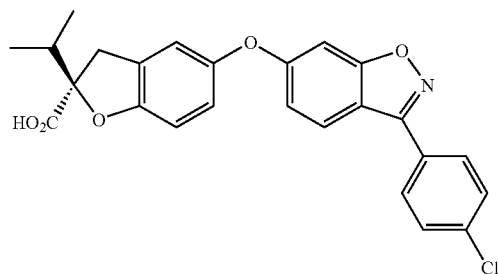
Example 18 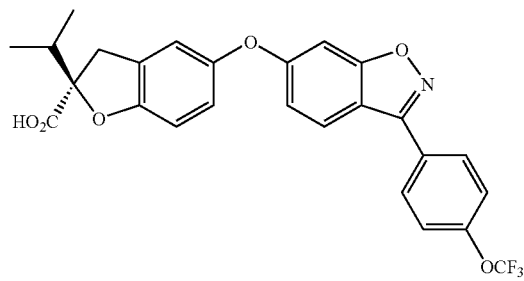
Example 19 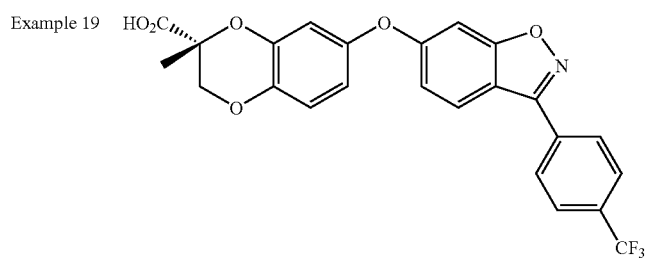
Example 20 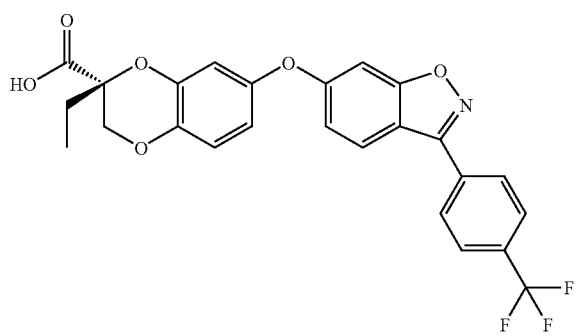
Example 21 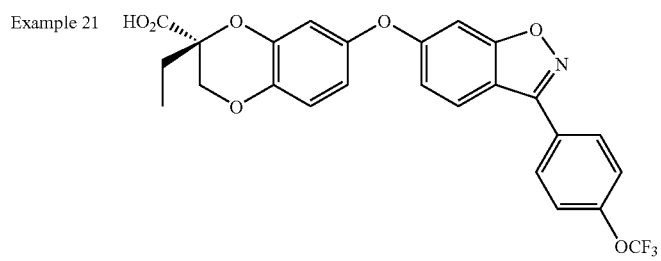
TABLE 2
Example 1: 2-Methyl-2-{3-[3-(4-trifluoromethyl-phenyl)-benzo[d]isoxazol-6-yloxy]-phenoxy}-propionic acid;
Example 2: 2-Methyl-2-{4-[3-(4-trifluoromethyl-phenyl)-benzo[d]isoxazol-6-yloxy]-phenoxy}-propionic acid;

TABLE 2-continued

Example 3: 2-Methyl-2-{3-[3-(4-trifluoromethoxy-phenyl)-benzo[d]isoxazol-6-yloxy]-phenoxy}-propionic acid;
Example 4: 2-Methyl-2-{3-[3-(4-chloro-phenyl)-benzo[d]isoxazol-6-yloxy]-phenoxy}-propionic acid;
Example 5: 2-Methyl-2-{3-[3-(4-isopropy-phenyl)-benzo[d]isoxazol-6-yloxy]-phenoxy}-propionic acid;
Example 6: 2-Methyl-2-{3-[3-(4-ethyl-phenyl)-benzo[d]isoxazol-6-yloxy]-phenoxy}-propionic acid;
Example 7: 2-Methyl-2-{3-[3-(3-trifluoromethyl-phenyl)-benzo[d]isoxazol-6-yloxy]-phenoxy}-propionic acid;
Example 8: 2-{3-[3-(4-trifluoromethyl-phenyl)-benzo[d]isoxazol-6-yloxy]-phenoxy}-propionic acid;
Example 9: 2-{3-[3-(4-chloro-phenyl)-benzo[d]isoxazol-6-yloxy]-phenoxy}-butanoic acid;
Example 10: 2-{3-[3-(4-trifluoromethyl-phenyl)-benzo[d]isoxazol-6-yloxy]-phenoxy}-butanoic acid;
Example 11: 3-Methyl-2-{3-[3-(4-trifluoromethyl-phenyl)-benzo[d]isoxazol-6-yloxy]-phenoxy}-butanoic acid;
Example 12: 2-{2-fluoro-3-[3-(4-trifluoromethyl-phenyl)-benzo[d]isoxazol-6-yloxy]-phenoxy}-butanoic acid;
Example 13: 2-{3-[3-(4-Dimethylamino-phenyl)-benzo[d]isoxazol-6-yloxy]-phenoxy}-2-methyl-propionic acid;
Example 14: 2-Ethyl-5-[3-(4-trifluoromethyl-phenyl)-benzo[d]isoxazol-6-yloxy]-2,3-dihydro-benzofuran-2-carboxylic acid;
Example 15: 2-Isopropyl-5-[3-(4-trifluoromethyl-phenyl)-benzo[d]isoxazol-6-yloxy]-2,3-dihydro-benzofuran-2-carboxylic acid;
Example 16: 2-Isopropyl-5-[3-(4-isopropyl-phenyl)-benzo[d]isoxazol-6-yloxy]-2,3-dihydro-benzofuran-2-carboxylic acid;
Example 17: 2-Isopropyl-5-[3-(4-chloro-phenyl)-benzo[d]isoxazol-6-yloxy]-2,3-dihydro-benzofuran-2-carboxylic acid;
Example 18: 2-Isopropyl-5-[3-(4-trifluoromethoxy-phenyl)-benzo[d]isoxazol-6-yloxy]-2,3-dihydro-benzofuran-2-carboxylic acid;
Example 19: 2-Methyl-7-[3-(4-trifluoromethyl-phenyl)-benzo[d]isoxazol-6-yloxy]-2,3-dihydro-benzo[1,4]dioxine-2-carboxylic acid;
Example 20: 2-Ethyl-7-[3-(4-trifluoromethyl-phenyl)-benzo[d]isoxazol-6-yloxy]-2,3-dihydro-benzo[1,4]dioxine-2-carboxylic acid; and
Example 21: 2-Ethyl-7-[3-(4-trifluoromethoxy-phenyl)-benzo[d]isoxazol-6-yloxy]-2,3-dihydro-benzo[1,4]dioxine-2-carboxylic acid.

The invention further includes pharmaceutical compositions comprising any of the compounds described above, including pharmaceutically acceptable salts, and a pharmaceutically acceptable carrier.

The invention includes pharmaceutical compositions containing a compound described herein, or a pharmaceutically acceptable salt, as the only active ingredient, and a pharmaceutically acceptable carrier. The invention also includes pharmaceutical compositions containing a compound described herein, or a pharmaceutically acceptable salt, and one or more other active ingredients, and a pharmaceutically acceptable carrier.

Definitions

"Alkyl", as well as other groups having the prefix "alk", such as alkoxy or alkenyl, means carbon chains which may be linear or branched, including chains with multiple branch points, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Isopropyl and sec- and tert-butyl are branched.

"Alkenyl" means carbon chains which contain at least one carbon-carbon double bond, and which may be linear or branched. Examples of alkenyl include vinyl, allyl, isopropenyl, pentenyl, hexenyl, heptenyl, 1-propenyl, 2-butenyl, 2-methyl-2-butenyl, and the like.

"Cycloalkyl" means a mono-or bicyclic saturated carbocyclic ring having from 3 to 10 carbon atoms, unless otherwise stated. The term also includes a monocyclic or bicyclic saturated carbocyclic ring which is fused to another cyclic group, such as an aryl group. Examples of cycloalkyl include cyclopropyl, cyclopentyl, cyclohexyl, cycloheptyl, and the like.

"Aryl" (and "arylene") when used to describe a substituent or group in a structure means a monocyclic or bicyclic or tricyclic group or substituent in which all of the rings are aromatic and which contains only carbon ring atoms. "Aryl" groups can be fused to other cyclic groups, such as a cycloalkyl or heterocyclic group. Examples of aryl substituents include phenyl and naphthyl. Phenyl is the preferred aryl group.

"Heterocycle" means a fully or partially saturated ring containing at least one heteroatom selected from N, S and O, where the ring has from 3 to 10 atoms, unless otherwise defined.

"Heteroaryl" (and "heteroarylene") means an aromatic ring containing at least one ring heteroatom selected from N, O and S (including SO and $SO_2$), where the ring contains 5-6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, and pyrazinyl. Heteroaryl and aromatic rings can be fused together to form bicyclic or tricyclic ring systems, as for example benzisoxazolyl, benzoxazolyl, benzothiazolyl, benzimidazolyl, benzofuranyl, benzothiophenyl (including S-oxide and dioxide), quinolyl, indolyl, isoquinolyl, dibenzofuran and the like.

"Halogen" includes fluorine, chlorine, bromine and iodine. Fluorine is generally the most preferred halogen substituent on an alkyl group.

"Me" and "Et" represent methyl and ethyl respectively.

The term "administration of" or "administering" a compound means providing a compound of this invention, or a pharmaceutically acceptable salt of a compound of this invention, or a prodrug of a compound of this invention to a patient in need of treatment.

To treat, as a disease or condition, means to deal with the disease or condition in a specified manner.

Amelioration of a disease or condition means improving the disease or condition or making it better.

"Metabolic Syndrome" is defined in the Third Report of the National Cholesterol Education Program Expert Panel on Detection, Evaluation and Treatment of High Blood Cholesterol In Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The "patient" to whom the compounds of this invention can be administered may be selected from mammals, including primates, such as monkeys and apes; bovines, such as cows; equines, such as horses; canines, such as dogs; felines, such as cats; ovines, such as goats and sheep; and rodents, such as mice, rats, and guinea pigs. Patients may also include non-mammalian species, such as chickens and other birds. The preferred patient is a human.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Optical Isomers—Diastereomers—Geometric Isomers—Tautomers

Compounds of Formula I may contain one or more asymmetric centers. The compounds can thus occur as racemic mixtures, single enantiomers, diastereomeric mixtures and individual diastereomers. The present invention is meant to comprehend all such isomeric forms of the compounds of Formula I. The invention specifically includes enantiomers and racemic mixtures of compounds that are shown having a stereochemical configuration, and the individual stereoisomers of compounds that are shown without a representation of stereochemistry.

Some of the compounds described herein contain olefinic double bonds, and unless specified otherwise, are meant to include both E and Z geometric isomers.

Some of the compounds described herein may exist with different points of attachment of hydrogen coupled with double bond shifts, referred to as tautomers. An example is a carbonyl (e.g. a ketone) and its enol form, often known as keto-enol tautomers. The individual tautomers as well as mixtures thereof are encompassed with compounds of Formula I.

If desired, racemic mixtures of compounds of Formula I may be separated by means of classical resolution through fractional crystallization of salts formed with enantiomerically pure acids or bases. Other diasteromeric derivatives can be formed by the coupling of a racemic mixture of the compounds of Formula I to an enantiomerically pure compound. Such diastereomeric mixture may be separated by standard chromatographic methods or recrystallization protocols. These diasteromeric derivatives may then be converted to the pure enantiomers of the compounds of Formula I by cleavage of the added chiral residue. The racemic mixture of the compounds of Formula I can also be separated directly by chromatographic methods utilizing chiral stationary phases, of which many examples are known in the literature.

Alternatively, any enantiomer of a compound of the general Formula I may be obtained by stereoselective synthesis using optically pure starting materials or reagents of known configuration.

Compounds of Formula I that have more than one asymmetric center and that occur as diasteromeric mixtures can similarly be separated into individual diastereomers by standard methods, and these can be separated to individual enantiomers as described above.

Salts

The term "pharmaceutically acceptable salts" refers to salts prepared from pharmaceutically acceptable non-toxic bases or acids including inorganic or organic bases and inorganic or organic acids. For the carboxylic acid compounds of Formula I, salts derived from inorganic bases include aluminum, ammonium, calcium, copper, ferric, ferrous, lithium, magnesium, manganous, manganic, potassium, sodium, and zinc salts and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

For compounds that are basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Prodrugs are compounds that are converted to the claimed compounds as they are being administered to a patient or after they have been administered to a patient. The prodrugs are compounds of this invention, and the active metabolites of the prodrugs, where the metabolites have Formula I, are also compounds of the invention. A non-limiting example of a prodrug of the carboxylic acids of this invention is an ester of the carboxylic acid, as for example a $C_1$ to $C_6$ ester, or an ester which has functionality that makes it more easily hydrolyzed after administration to a patient.

Examples of prodrugs of this class of compounds include compounds in which the carboxy group —C(=O) in Formula I is of the form —C(=O)G, where G is a group that is easily removed under physiological conditions during or after administration to a mammalian patient to yield the free carboxylic acid or carboxylate salt thereof.

Examples of prodrugs of Formula Ia include compounds in which G is selected from the group consisting of —OR$^a$, —OCH$_2$OR$^a$, —OCH(CH$_3$)OR$^a$, —OCH$_2$OC(O)R$^a$, —OCH(CH₃)OC(O)R$^a$, —OCH₂OC(O)OR$^a$, —OCH(CH₃)OC(O)OR$^a$, and —NR$^b$R$^b$, where each R$^a$ is independently selected from C$_{1-6}$ alkyl which is optionally substituted with one or two groups selected from —CO₂H, —CONH₂, —NH₂, —OH, —OAc, —NHAc, and phenyl; and wherein each R$^b$ is independently selected from H and R$^a$.

Utilities

Compounds of the present invention are potent agonists of the peroxisome proliferator activated receptor subtypes, particularly PPARα, generally with little or no activity with respect to PPARγ or PPARδ. Compounds of the present invention are thus selective and potent agonists of the subtype PPARα. A few of the compounds also have activity as agonists of PPARγ and/or PPARδ. Compounds of the present invention are useful in treating, controlling or ameliorating diseases, disorders and conditions, where the treatment, control or amelioration is effected by the activation of the PPARα subtype.

An important aspect of this invention is that it provides a method for the treatment, control, or amelioration of various lipid disorders, including dyslipidemia, hypercholesterolemia, hyperlipidemia, hypertriglyceridemia, low HDL levels, high LDL levels, and atherosclerosis and its sequelae, which comprises administering to a mammal in need of such treatment a therapeutically effective amount of a compound having formula I.

The compounds as defined herein may be used in treating or controlling or ameliorating one or more of the following diseases or conditions in a mammalian or human patient in need of treatment, where the treatment comprises the administration of a therapeutically effective amount of a compound of Formula I to the patient in need of treatment:

(1) lipid disorders;
(2) hyperlipidemia;
(3) low IDL-cholesterol;
(4) high LDL-cholesterol;
(5) hypercholesterolemia;
(6) hypertriglyceridemia;
(7) dyslipidemia, including high LDL cholesterol and low HDL cholesterol; and
(8) atherosclerosis, including sequelae of atherosclerosis (angina, claudication, heart attack, stroke, etc.).

More generally, compounds having Formula I, Ia, Ib, and Ic may be used to treat or control or ameliorate one or more of the following diseases, disorders and conditions, by the administration of a therapeutically effective amount of a compound of the compound: (1) lipid disorders, (2) dyslipidemia, (3) hyperlipidemia, (4) hypertriglyceridemia, (5) hypercholesterolemia, (6) low HDL levels, (7) high LDL levels, (8) atherosclerosis and its sequelae, (9) obesity, including abdominal obesity (10) vascular restenosis, (11) retinopathy, (12) non-insulin dependent diabetes mellitus (NIDDM), (13) hyperglycemia, (14) impaired glucose tolerance, (15) insulin resistance, (16) irritable bowel syndrome, (17) inflammatory bowel disease, including Crohn's disease and ulcerative colitis, (18) pancreatitis, (19) other inflammatory conditions, (20) neurodegenerative disease, (21) Alzheimer's disease, (22) psoriasis, (23) acne vulgaris, (24) other skin diseases and dermatological conditions modulated by PPAR, (25) high blood pressure, (26) cachexia, and (27) the metabolic syndrome, sometimes known as Syndrome X.

The compounds may also be useful in the treatment of (1) neoplastic conditions, (2) adipose cell tumors, (3) adipose cell carcinomas, such as liposarcoma, (4) prostate cancer and other cancers, including gastric, breast, bladder and colon cancers, and (5) angiogenesis.

Other conditions which may be treated with the compounds of this invention include ovarian hyperandrogenism (polycystic ovarian syndrome), cachexia, and other disorders where insulin resistance is a component.

The present invention is further directed to the use of a compound of Formula I, or a pharmaceutically acceptable salt thereof, in the manufacture of a medicament that is useful for the treatment of a disease or condition that is treated by the administration of a PPARα agonist.

Another aspect of the invention provides a method of treating cachexia. PPARα is known to be necessary for an appropriate energy sparing response to starvation, and inappropriate metabolism and energy utilization is clearly responsible for the wasting of cachexia. The compounds of this invention may therefore be useful in the treatment of cachexia.

In another aspect, the invention provides a method of treating inflammatory conditions, including inflammatory bowel disease, Crohn's disease, and ulcerative colitis, by administration of an effective amount of a PPARα agonist of Formula I. Additional inflammatory diseases that may be treated with the instant invention include gout, rheumatoid arthritis, osteoarthritis, multiple sclerosis, asthma, ARDS, psoriasis, vasculitis, ischemia/reperfusion injury, and related diseases.

Another aspect of the invention provides a method of treating a variety of skin diseases and dermatological conditions that are modulated by PPARα agonists by administering an effective amount of a compound of Formula I to a mammalian or human patient in need of such treatment. These diseases and conditions include psoriasis and acne vulgaris. Examples of other skin diseases and dermatological disorders that may be treated include eczema; lupus associated skin lesions; dermatitides such as seborrheic dermatitis and solar dermatitis; keratoses such as seborrheic keratosis, senile keratosis, actinic keratosis, photo-induced keratosis, and keratosis follicularis; keloids and prophylaxis against keloid formation, warts including verruca, condyloma, or condyloma accuminatum, and human papilloma viral (HPV) infections such as venereal warts, viral warts, molluscum contagiosum, leukoplakia, lichen planus, keratitis, skin cancer such as basal cell carcinoma, cutaneous T cell lymphoma and localized benign epidermal tumors (keratoderma, epidermal naevi).

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating hypertriglyceridemia, hypercholesterolemia, dyslipidemia, hyperlipidemia, and other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 100 milligrams. In the case of a 70 kg adult human, the total daily dose will generally be from about 1 milligram to about 350 milligrams. This dosage regimen will vary depending on the specific compound and also the patient. The dosage may be adjusted within the ranges recited above or even outside those ranges in order to provide the optimal therapeutic response. Examples of daily human doses are 1, 2.5, 5, 7.5, 10, 15, 25, 40, 50, 75, 100, 150, 200, 250, 300, and 350 mg.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt or prodrug thereof as an active ingredient, as well as a pharmaceutically acceptable carrier and optionally other therapeutic ingredients. More typically, a selected compound of Formula I, or a pharmaceutically acceptable salt thereof, will be the only active ingredient in a composition. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; an excipient such as mannitol, microcrstalline cellulose, or dicalcium phosphate; a disintegrating agent such as corn starch, potato starch, alginic acid or croscarmellose sodium; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

The compounds of this invention may be used in combination with other drugs that may also have utility in the treatment of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

For example, the compounds of Formula I may be administered in combination with one or more other lipid lowering drugs, including (1) a cholesterol biosynthesis inhibitor, including but not limited to, an HMG-CoA reductase inhibitor, such as lovastatin, simvastatin, pravastatin, fluvastatin, atorvastatin, rivastatin, itavastatin, rosuvastatin, and ZD-4522; (2) a cholesterol absorption inhibitor (for example a stanol ester, a sterol glycoside such as tiqueside, or an azetidinone such as ezetimibe); (3) an ACAT inhibitor (such as avasimibe), (4) niacin; (5) a bile acid sequestrant; (6) a microsomal triglyceride transport inhibitor; (7) a bile acid reuptake inhibitor; (8) a PPARα/γ agonist, such as muraglitazar; and (9) a CETP inhibitor, such as torcetrapib. These combination treatments are expected to be particularly effective for the treatment or control of one or more lipid disorders or conditions selected from dyslipidemia, hypercholesterolemia, hyperlipidemia, hypertriglyceridemia, low HDL levels, high LDL levels, and atherosclerosis and its sequelae. The combination therapy may make it possible to achieve therapeutic control using a reduced amount of one or both active ingredients and/or to achieve better lipid control than would be expected based on the control that is achieved when either of the compounds is used alone. The combination therapy may make it possible to achieve therapeutic control of one or more lipid disorders and diabetes. Preferred combinations include a compound of Formula I and one or more other compounds selected from a cholesterol absorption inhibitor, such as ezetimibe, a statin (e.g. simvastatin, atorvastatin, or rosuvastatin), an ACAT inhibitor, or another PPARα agonist, such as fenofibrate or another fibrate. Highly preferred combinations include combinations consisting essentially of a compound of this invention with a cholesterol absorption inhibitor (ezetimibe), or a compound of this invention with a statin (eg simvastatin), or a compound of this invention with both a statin and a cholesterol asorption inhibitor.

More generally, examples of therapeutic classes of compounds that may be administered in combination with a compound of Formula I, either separately or in the same pharmaceutical composition, include, but are not limited to:
(a) insulin sensitizers;
(b) antidiabetic compounds;
(c) cholesterol lowering agents;
(d) antiobesity compounds;
(e) anti-inflammatory compounds; and
(f) antihypertensives.

Examples of classes of compounds that may be administered in combination with compounds having Formula I include:
(a) PPARγ agonists and partial agonists, such as the glitazones (e.g. troglitazone, pioglitazone, englitazone, MCC-555, rosiglitazone, and the like);
(b) PPARα/γ dual agonists, such as muraglitazar;
(c) other PPARα agonists, such as fenofibric acid derivatives, including gemfibrizol, clofibrate, fenofibrate, and bezafibrate,
(d) PPARδ agonists such as those disclosed in WO97/28149;
(e) biguanides, such as metformin and phenformin;
(f) protein tyrosine phosphatase-1B (PTP-1B) inhibitors;
(g) dipeptidyl peptidase IV (DP-IV) inhibitors, such as sitagliptin, vildagliptin, and saxagliptin;
(h) insulin or insulin mimetics;
(i) sulfonylureas, such as tolbutamide and glipizide, or related materials;
(j) α-glucosidase inhibitors (such as acarbose);
(k) glucagon receptor antagonists;
(l) glycogen phosphorylase inhibitors;
(m) 11-Beta-HSD type 1 enzyme inhibitors;
(n) 11-Beta-HSD type 1 receptor antagonists;
(o) exendin-4, exendin-3, GLP-1, GLP-1 mimetics, and GLP-1 receptor agonists, such as exenatide and those disclosed in WO00/42026 and WO00/59887;
(p) GIP, GIP mimetics such as those disclosed in WO00/58360, and GIP receptor agonists;
(q) PACAP, PACAP mimetics, and PACAP receptor 3 agonists such as those disclosed in WO 01/23420;
(r) HMG-CoA reductase inhibitors (lovastatin, simvastatin, pravastatin, fluvastatin, atorvastatin, rivastatin, itavastatin, rosuvastatin, ZD-4522, and other statins);
(s) Bile acid sequestrants (cholestyramine, colestipol, and dialkylaminoalkyl derivatives of a cross-linked dextran);
(t) nicotinyl alcohol, nicotinic acid or a salt thereof;
(u) ezetimibe and other inhibitors of cholesterol absorption;
(v) acyl CoA:cholesterol acyltransferase inhibitors (ACAT inhibitors); such as for example avasimibe;
(w) phenolic anti-oxidants, such as probucol;
(x) ileal bile acid transporter inhibitors;
(y) agents intended for use in the treatment of inflammatory conditions such as aspirin, non-steroidal anti-inflammatory drugs, glucocorticoids, azulfidine, and cyclooxygenase 2 selective inhibitors;
(z) antiobesity compounds such as fenfluramine, dexfenfluramine, phentermine, sibutramine, orlistat, neuropeptide Y5 inhibitors, and β3 adrenergic receptor agonists;
(aa) thyroid hormone mimetics;
(bb) LXR agonists;
(cc) FXR agonists;
(dd) PLTP inhibitors;
(ee) CETP inhibitors, such as torcetrapib;
(ff) glucocorticoids; and
(gg) TNF sequestrants.

The above combinations will generally include combinations of one compound of the present invention with one other active compound. However, it is contemplated that combinations may also include more than two active ingredients, selected from one or more compounds of the present invention and one or more other active compounds listed above. Non-limiting examples include combinations of one or more compounds having Formula I with two or more active compounds selected from insulin sensitizers; antidiabetic compounds; cholesterol lowering agents; antiobesity compounds; anti-inflammatory compounds; and antihypertensives.

Examples of combinations that may be appropriate for patients having Type 2 diabetes accompanied by dyslipidemia include one or more compounds having Formula I and one or more compounds selected from anti-diabetic compounds, including biguanides, sulfonylureas, PPARγ agonists, PTP-1B inhibitors, DP-IV inhibitors, insulin, and antiobesity compounds.

Biological Assays

A) PPAR Binding Assays

For preparation of recombinant human PPARγ, PPARδ, and PPARα: Human PPARγ$_2$, human PPARδ and human PPARα were expressed as gst-fusion proteins in *E. coli*. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). *E. coli* containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C.

For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamidine and 0.5 mM PMSF) containing 0.1% non-fat dry milk and 10 nM [$^3$H$_2$] AD5075, (21 Ci/mmole), ±test compound as described in Berger et al (Novel peroxisome proliferator-activated receptor (PPARγ) and PPARδ ligands produce distinct biological effects. J. Biol. Chem. (1999), 274: 6718-6725.) Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3$H$_2$]L-783483, (17 Ci/mmole), ±test compound as described in Berger et al (Novel peroxisome proliferator-activated receptory (PPARγ) and PPARδ ligands produce distinct biological effects. 1999 J Biol Chem 274: 6718-6725). (L-783483 is 3-chloro-4-(3-(7-propyl-3-trifluoromethyl-6-benz-[4,5]-isoxazoloxy)propylthio)phenylacetic acid, Ex. 20 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 5.0 nM [$^3$H$_2$](3-(4-(3-phenyl-7-propyl-6-benz-[4,5]-isoxazoloxy)butyloxy))phenylacetic acid (34 Ci/mmole), ±test compound. This is a tritium labelled variant of Ex.62 in WO 97/28137. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

B). Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5×)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at 12×10$^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% CO$_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 μg of pUAS(5×)-tk-luc reporter vector and 0.0002 μg of pCMV-lacZ as an internal control for transactivation efficiency. Cells were incubated in the transfection mixture for 5 h at 37° C. in an atmosphere of 10% CO$_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate ±increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

C. In Vivo Studies

Male db/db mice (10-11 week old C57B1/KFJ, Jackson Labs, Bar Harbor, Me.) are housed 5/cage and allowed ad lib. access to ground Purina rodent chow and water. The animals, and their food, are weighed every 2 days and are dosed daily by gavage with vehicle (0.5% carboxymethylcellulose) ±test compound at the indicated dose. Drug suspensions are prepared daily. Plasma glucose, and triglyceride concentrations are determined from blood obtained by tail bleeds at 3-5 day intervals during the study period. Glucose and triglyceride determinations are performed on a Boehringer Mannheim Hitachi 911 automatic analyzer (Boehringer Mannheim, Indianapolis, Ind.) using heparinized plasma diluted 1:6 (v/v) with normal saline. Lean animals are age-matched heterozygous mice maintained in the same manner.

Male Golden Syrian hamsters weighing ~150 g are used to measure lipid modulation effects of test compounds. Hamsters are housed in boxes (5 per box), are fed a normal rodent chow diet, and are given free access to water. Compounds are suspended in 0.5% methylcellulose and gavaged daily to the hamsters for 9 days (10 hamsters per group). On the morning of the 10$^{th}$ day, the hamsters are euthanized with carbon dioxide, and blood samples are obtained via heart puncture. Serum levels of total cholesterol and triglycerides are determined.

Mature male beagle dogs, weighing ~15 kg on average, are used to measure the lipid modulation effects of test compounds. Dogs are housed individually, are fed a cholesterol-free chow diet, and are given free access to water. Prior to the start of experiments, samples are taken weekly from the jugular vein and the serum cholesterol levels are determined. To test the effects of compounds on serum cholesterol, compounds are suspended in 0.5% methylcellulose and gavaged daily to the dogs for 2 weeks (5 dogs per group). Blood samples are taken during and after the dosing period, and serum levels of total cholesterol and triglycerides are determined.

Synthetic Methods

The Process for making the compounds of the instant invention is generally depicted in Scheme 1 below.

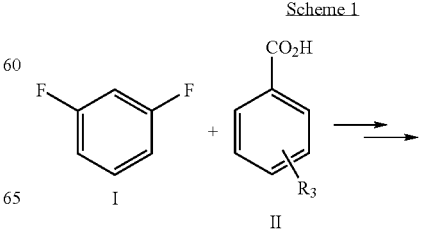

Scheme 1

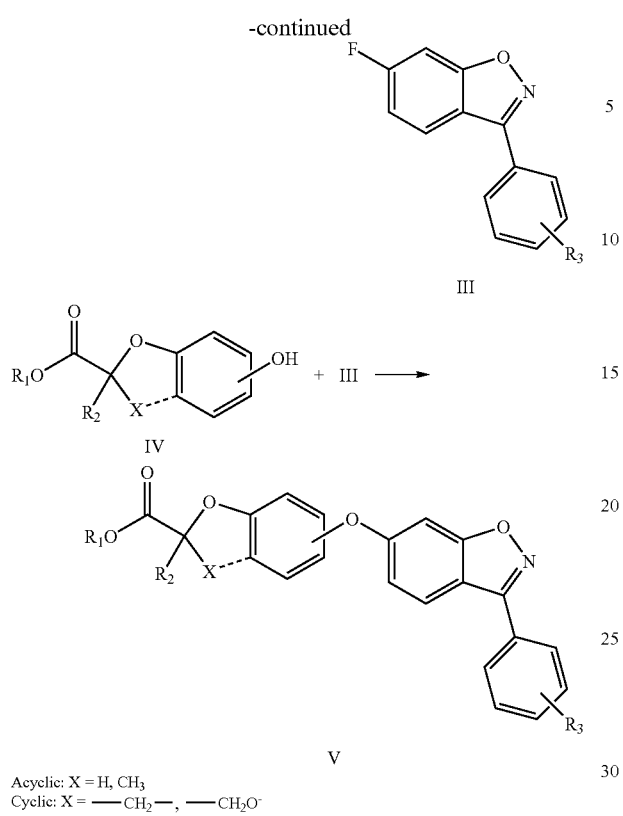

Acyclic: X = H, CH₃
Cyclic: X = —CH₂—, —CH₂O⁻

The appropriately substituted substituted 6-fluorobenzo[d]isoxazoles of formula III may be synthsized by the Friedel-Crafts reaction between 1,3-difluorobenzene and substituted benzoyl chloride followed by the formation of the isoxazole ring. Various methods were used for the preparation of the phenol intermediates of formula IV. The assembly of the final compound of formula V was performed by the displacement of fluoride of compound of formula III with the phenol of formula IV in the presence of an inorganic base, e.g. cesium carbonate, in an aprotic polar solvent, e.g. N,N-dimethylacetamide. The desired acid form of formula V may be obtained by ester hydrolysis under aqueous basic conditions.

General Procedure 1 for the Preparation of 6-fluoro-3-(substituted phenyl)-benzo[d]-isoxazole Step 1. 1,3-difluorobenzene (3.42 g, 30 mmol) and substituted benzoyl chloride (10 mmol) were dissolved in trifluoromethanesulfonic acid (5.0 mL). The resulting solution was heated at 60° C. for 1 h and then diluted with ethyl acetate (100 mL) and successively washed with water (2×50 mL) and saturated aqueous NaHCO₃. The organic phase was dried and concentrated to give essentially pure substituted 2',4'-difluorobenzophenone.

Step 2. The benzophenone product from Step 1 (10 mmol), hydroxyamine hydrochloride (3.0 g, 50 mmol) and sodium acetate (4.1 g, 5 mol) were mixed in methanol (50 mL) and the resulting suspension was stirred at 50° C. for 6 h. Methanol was removed and the residual solid was triturated with ethyl acetate. The mixture was filtered through a short path of silica gel and the filtrate was concentrated. The residue, consisting of a Z/E mixture of oximes, was dissolved in anhydrous DMF (50 mL) and Cs₂CO₃ (6.5 g, 20 mml) was added to the solution. After being stirred at 80° C. for 14 h, the mixture was diluted with ethyl acetate, washed with water and dried over MgSO₄. After removal of solvents, the residue was purified by chromatography on silica gel to give 6-fluoro-3-(substituted phenyl)-benzo[d]isoxazole in 70-95% overall yield (two steps).

Intermediate 1

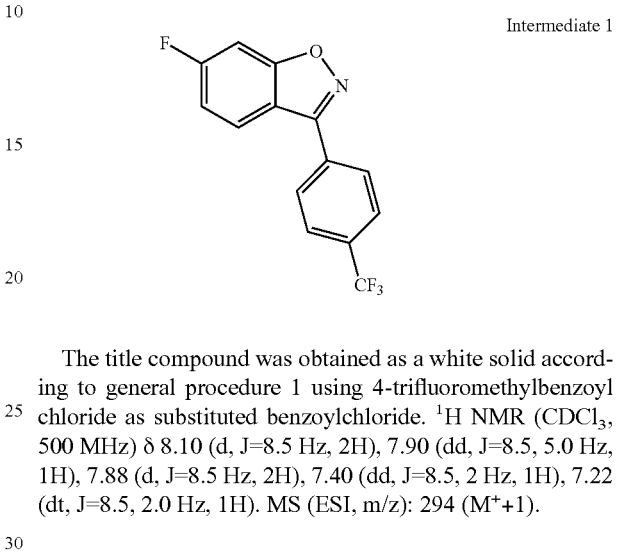

The title compound was obtained as a white solid according to general procedure 1 using 4-trifluoromethylbenzoyl chloride as substituted benzoylchloride. ¹H NMR (CDCl₃, 500 MHz) δ 8.10 (d, J=8.5 Hz, 2H), 7.90 (dd, J=8.5, 5.0 Hz, 1H), 7.88 (d, J=8.5 Hz, 2H), 7.40 (dd, J=8.5, 2 Hz, 1H), 7.22 (dt, J=8.5, 2.0 Hz, 1H). MS (ESI, m/z): 294 (M⁺+1).

Intermediate 2

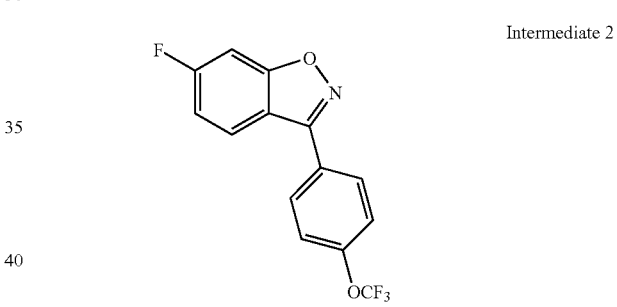

The title compound was obtained as a white solid according to general procedure 1 using 4-trifluoromethoxybenzoyl chloride as substituted benzoylchloride. ¹H NMR (CDCl₃, 500 MHz) δ 7.90 (d, J=8.5 Hz, 2H), 7.85 (dd, J=8.5, 5.0 Hz, 1H), 7.80 (d, J=8.5 Hz, 2H), 7.40 (dd, J=8.5, 2 Hz, 1H), 7.22 (dt, J=8.5, 2.0 Hz, 1H).

Intermediate 3

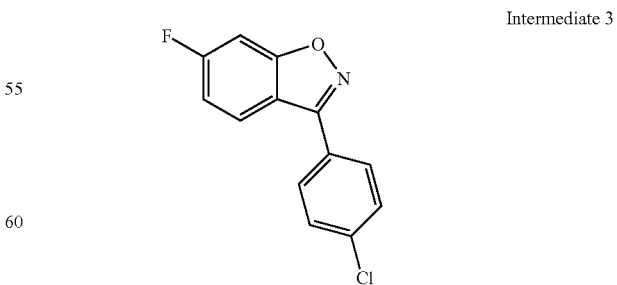

The title compound was obtained as a white solid according to general procedure 1 using 4-chlorobenzoyl chloride as substituted benzoylchloride. ¹H NMR (CDCl₃, 500 MHz) δ

7.85 (d, J=8.5 Hz, 2H), 7.80 (dd, J=8.5, 5.0 Hz, 1H), 7.70 (d, J=8.5 Hz, 2H), 7.35 (dd, J=8.5, 2 Hz, 1H), 7.12 (ddd, J=8.5, 8.5, 2.0 Hz, 1H).

Hz, 1H), 7.31 (dt, J=8.9, 2.2 Hz, 1H). MS (ESI, m/z): 282.0 (M$^+$+1).

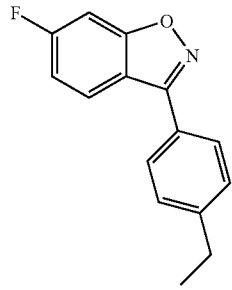

Intermediate 4

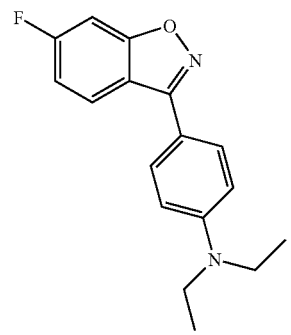

Intermediate 7

The title compound was obtained as a white solid according to general procedure 1 using 4-ethylbenzoyl chloride as substituted benzoylchloride. $^1$H NMR (CDCl$_3$, 500 MHz) δ 7.86 (d, J=8.5 Hz, 2H), 7.80 (dd, J=8.5, 5.0 Hz, 1H), 7.40 (d, J=8.5 Hz, 2H), 7.25 (dd, J=8.5, 2 Hz, 1H), 7.22 (ddd, J=8.5, 2.0 Hz, 1H), 2.74 (q, J=7.8 Hz, 2H), 1.28 (t, J=7.8 Hz, 3H).

The title compound was obtained as a white solid according to general procedure 1 using 4-(dimethylamino)benzoyl chloride as substituted benzoylchloride.

General Procedure 2 for the Preparation of Substituted Phenol Intermediates

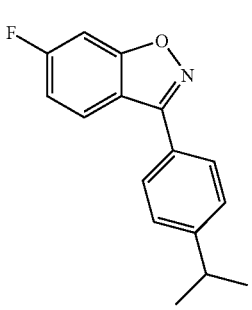

Intermediate 5

Step 1. 3-Benzyloxyphenol (4.0 g, 20 mmol) and 2-bromoalkanoate (40 mmol) and Cs$_2$CO$_3$ (14.3 g, 40 mmol) in DMF (100 mL) was stirred at 60° C. for 2-8 hrs. The reaction mixture was diluted with ethyl acetate and washed with water. The organic phase was dried over MgSO$_4$ and concentrated. The residue was purified by chromatography on silica gel eluting with 9:1 (v/v) hexane/ethyl acetate to afford 2-(benzyloxyphenoxy)alkanoate.

Step 2. The product from step 1 was dissolved in ethyl acetate and the solution was stirred in the presence of 10% Pd—C under hydrogen (1 atm) for 3 h. The reaction mixture was filtered through a pad of celite and concentrated to afford the title compound as a colorless oil.

The title compound was obtained as a white solid according to general procedure 1 using 4-isopropylbenzoyl chloride as substituted benzoylchloride. $^1$H NMR (500 MHz, CD$_3$OD) δ 7.87 (d, J=8.5 Hz, 2H), 7.80 (dd, J=8.5, 5.0 Hz, 1H), 7.40 (d, J=8.5 Hz, 2H), 7.25 (dd, J=8.5, 2 Hz, 1H), 7.22 (ddd, J=8.5, 2.0 Hz, 1H), 3.0 (m, 1H), 1.30 (d, J=7.0 Hz, 6H).

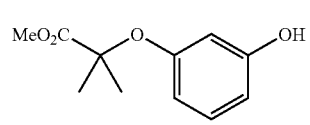

Intermediate 8

Intermediate 6

The title compound was obtained as an oil according to general procedure 2 using methyl 2-bromo-2-methylpropionate as 2-bromoalkanoate. $^1$H NMR (500 MHz, CDCl$_3$) δ 7.14 (t, J=8.0 Hz, 1H), 6.50 (m, 1H), 6.41 (m, 1H), 6.39 (t, J=2.0 Hz, 1H), 3.80 (s, 3H), 1.62 (s, 6H).

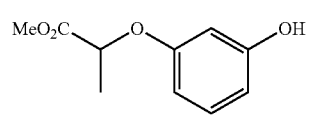

Intermediate 9

The title compound was obtained as a white solid according to general procedure 1 using 3-trifluoromethylbenzoyl chloride as substituted benzoylchloride. $^1$H NMR (500 MHz, CD$_3$OD) δ 8.25 (m, 2H), 8.05 (dd, J=8.7, 5.0 Hz, 1H), 7.91 (br d, J=8.0 Hz, 1H), 7.83 (t, J=7.8 Hz, 1H), 7.55 (dd, J=8.6, 2.2

The title compound was obtained as an oil according to general procedure 2 using methyl 2-bromopropionate as 2-bromoalkanoate. $^1$H NMR (500 MHz, CDCl$_3$) δ 7.14 (t, J=9.0 Hz, 1H), 6.47 (dd, J=15 Hz, 2.5 Hz, 1H), 6.47 (s, 1H), 6.42 (t, J=2.5 Hz, 1H), 4.77 (q, J=6.5 Hz, 1H), 3.79 (s, 3H), 1.63 (d, J=6.5 Hz, 3H).

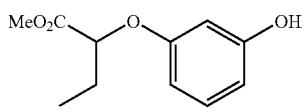

Intermediate 10

The title compound was obtained as an oil according to general procedure 2 using methyl 2-bromo-2-butanoate as 2-bromoalkanoate.

¹H NMR (500 MHz, CDCl₃) δ 7.14 (t, J=8.0 Hz, 1H), 6.48 (m, 2H), 6.43 (t, J=2.5 Hz, 1H), 4.48 (t, J=6.5 Hz, 1H), 3.78 (s, 3), 2.0 (m, 2H), 1.09 (t, J=6.5 Hz, 3H).

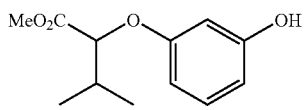

Intermediate 11

The title compound was obtained as an oil according to general procedure 2 using methyl 2-bromo-3-methylbutanoate as 2-bromoalkanoate.

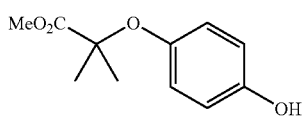

Intermediate 12

The title compound was obtained as an oil according to general procedure 2 using methyl 2-bromo-2-methylpropionate as 2-bromoalkanoate and 4-benzyloxyphenol instead of 3-benzyloxyphenol. ¹H NMR (500 MHz, CDCl₃) δ 7.02 (d, J=7.0, 2H), 6.69 (d, J=7.0, 2H), 3.80 (s, 3H), 1.59 (s, 6H).

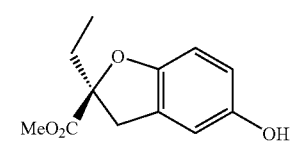

Intermediate 13

Intermediate 13 was prepared by following the steps described below.

Step 1.
ethyl(E)-2-ethyl-3-(2-fluorophenyl)propenoate

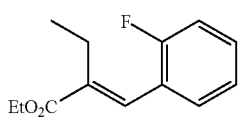

A solution of 2-fluorobenzaldehyde (6.2 g, 50 mmol) and ethyl 2-(triphenylphosphoranylidene)butanoate (18.8 g, 50 mmol) in THF (200 mL) was refluxed for 2 hrs. The reaction mixture was concentrated and the residue was triturated with 1:1 hexane:ethyl acetate. The precipitate was removed by filtration through silica gel and the filtrate was concentrated. The residue was purified by chromatography on silica gel eluting with 8:2 hexane:ethyl acetate to give ethyl (E)-2-ethyl-3-(2-fluorophenyl)propenoate.

Step 2. ethyl(2S,3S)-2-ethyl-3-(2-fluorophenyl)-2,3-dihydroxypropanoate

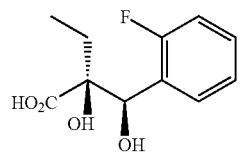

The product from Step 1 (4.4 g, 20 mmol), AD-mix-β(28.0 g) and methylsulfonamide (1.9 g, 2.0 mmol) were mixed in 1:1 t-BuOH:H₂O (200 mL). The resulting mixture was stirred at 4° C. for 2 days and quenched by addition of an aqueous solution of Na₂SO₃ (2 N, 20 mL). The mixture was diluted with ethyl acetate (200 mL), washed with brine (2×100 mL) and dried. Removal of solvent gave ethyl(2S,3S)-2-ethyl-3-(2-fluorophenyl)-2,3-dihydroxypropanoate with 97% ee, as determined by HPLC on a Chiracel OD column using 30% isopropanol in heptane as the mobile phase.

¹H NMR (500 MHz, CDCl₃) δ 7.57 (dt, J=8.0, 2.0 Hz, 1H), 7.31 (m, 1H), 7.19 (m, 1H), 7.05 (m, 1H), 5.30 (s, 1H), 4.38 (m, 2H), 1.84 (m, 1H), 1.38 (t, J=7.5 Hz, 3H), 1.25 (m, 1H), 0.79 (t, J=7.5 Hz, 3H).

Step 3. (2S)-2-Ethyl-2-hydroxy-3-(2-fluorophenyl)propanoic acid

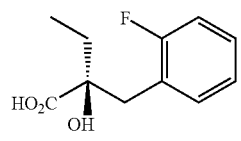

The product from Step 2 (5.2 g, 20 mmol), 10% palladium on carbon (2.5 g) and concentrated sulfuric acid (0.53 mL, 10 mmol) were mixed in acetic acid (100 mL). The reaction mixture was hydrogenated at 45 psi for 48 hrs. Sodium acetate (1.7 g, 20 mmol) was added and the reaction mixture was stirred for 10 min before it was filtered through silica gel. Concentration of the filtrate gave essentially pure ethyl(2S)-2-ethyl-2-hydroxy-3-(2-fluorophenyl)propanoate. The ethyl ester was hydrolyzed with KOH (2 N, 25 mL) in methanol (150 mL) to give the title compound as a white solid.

¹H NMR (600 MHz, CDCl₃) δ 7.22-7.30 (m, 2H), 7.08 (t, J=7.8 Hz, 1H), 7.03 (dd, J=7.8, 9.0 Hz, 1H), 3.17 (d, J=14.0 Hz, 1H), 3.08 (d, J=14 Hz, 1H), 2.03 (dq, J=13.8, 7.8 Hz, 1H), 1.76 (dq, J=13.8, 7.8 Hz, 1H), 0.97 (t, J=7.8 Hz, 3H).

Step 4. Methyl(2S)-2-ethyl-2,3-dihydro-1-benzofuran-2-carboxylate

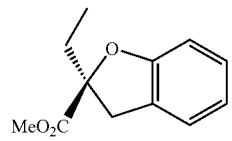

To a solution of the product from Step 3 (4.0 g, 20 mmol) in 1:4 DMF/toluene (100 mL) was added 60% NaH in mineral oil (1.76 g, 44 mmol) in 3 portions. The reaction mixture was stirred at 110° C. under $N_2$ for 4 hrs. The reaction was cooled to room temperature and poured into cold water (100 mL). The aqueous layer was washed with hexane (50 mL), acidified with 2 N aqueous HCl and extracted with ethyl acetate (3×50 mL). The extracts were washed with brine (50 mL), dried and concentrated. The residue was dissolved in 7:1 benzene/MeOH (80 mL) and treated with TMSCHN$_2$ (1M in hexane) until gas evolution ceased. The reaction was concentrated and the residue was chromatographed on silica gel eluting with 85:15 hexane:ethylacetate to give the title compound $^1$H NMR (500 MHz, CDCl$_3$) δ 7.16 (m, 2H), 6.90 (m, 2H), 3.80 (s, 3H), 3.60 (d, J=16 Hz, 1H), 3.23 (d, J=16 Hz, 1H), 2.12 (m, 1H), 2.02 (m, 1H), 1.02 (t, J=7.5 Hz, 3H).

Step 5 Methyl(2S)-5-acetyl-2-ethyl-2,3-dihydro-1-benzofuran-2-carboxylate

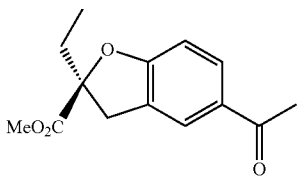

The product from Step 4 (3.1 g, 15 mmol) was mixed with acetyl chloride (3.5 g, 45 mmol) and aluminum chloride (6.0 g, 45 mmol) in dichloromethane (100 mL). The reaction mixture was stirred at 25° C. for 1 hr and then poured into 1 N aqueous HCl (100 mL). The organic layer was separated and the aqueous phase was extracted with dichloromethane (50 mL). The combined extracts were washed with brine and concentrated to give the title compound, which was used directly for the next step.

Step 6. The product from Step 5 (3.8 g, ca. 15 mmol), m-chloroperbenzoic acid (70%, 7.7 g, 30 mmol) and NaHCO$_3$ (3.8 g, 45 mmol) in dichloromethane (150 mL) was stirred under reflux for 2 hrs. The reaction mixture was washed successively with saturated aqueous sodium sulfite (100 mL) and aqueous NaHCO$_3$ (2×100 mL). After removal of solvent, the residue was dissolved in methanol (100 mL) and treated with aqueous KOH (5 N, 3 mL) at 0° C. for 5 min. The reaction was neutralized with acetic acid, filtered and concentrated. The residue was purified by chromatography on silica gel eluting with 8:2 hexane:ethyl acetate to give intermediate 13 as a white solid.

$^1$H NMR (500 MHz, CDCl$_3$) δ 6.72 (d, J=8.5 Hz, 1H), 6.67 (d, J=3 Hz, 1H), 6.61 (dd, J=8.5, 3.0, 1H), 3.80 (s, 3H), 3.54 (d, J=14.0 Hz, 1H), 3.16 (d, J=14.0 Hz, 1H), 2.05 (m, 2H), 1.0 (t, J=7.5 Hz, 3H). MS (ESI, m/z): 223 (M$^+$+1).

Intermediate 14

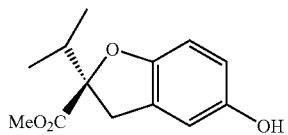

Intermediate 14 was prepared by following the steps described below.

Step 1. (2S)-2-Isopropyl-2-hydroxy-3-(2-fluorophenyl)propanoic acid

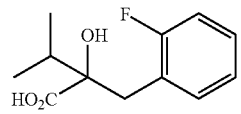

A solution of (o-fluorobenzyl)magnesium bromide in diethyl ether (100 mL), prepared from the corresponding o-fluorobenzyl bromide (9.45 g, 50.0 mmol) and magnesium turnings (1.32 g, 55.0 mmol), was added to a solution of ethyl 3-methyl-2-oxobutanoate (7.2 g, 50 mmol) in diethyl ether (50 mL) cooled at −78° C. After 30 min at −78° C., the reaction mixture was warmed to 0° C. and poured into saturated aqueous NH$_4$Cl. The organic layer was washed with brine, dried and concentrated. The residue was dissolved in methanol (200 mL) and kept with 2 N KOH (75 mL) for 2 hrs. at 50° C. The reaction mixture was diluted with water and washed with hexane. The aqueous layer was acidified with 2 N HCl, saturated with sodium chloride and extracted with ethyl acetate. Removal of solvents gave the title compound.

$^1$H NMR (500 MHz, CDCl$_3$) δ 7.30-7.35 (m, 1H), 7.18-7.23 (m, 1H), 7.06 (t, J=7.8 Hz, 1H), 7.00 (dd, J=7.8, 9.0 Hz, 1H), 3.17 (d, J=14.0 Hz, 1H), 3.05 (d, J=14.0 Hz, 1H), 2.18 (m, 1H), 1.1 (t, J=7.5 Hz, 3H), 0.90 (t, J=7.5 Hz, 3H).

Step 2. The product from Step 1 was converted to the racemate of intermediate 14 following the same procedures as described in Step 4, 5 and 6 for the preparation of intermediate 13. The racemate was separated on a preparative Chiracel OD column eluting with 10:90 isopropanol/heptane. The late fraction was collected and concentrated to afford intermediate 14 as an oil.

$^1$H NMR (500 MHz, CDCl$_3$) δ 6.72 (d, J=8.5 Hz, 1H), 6.67 (d, J=3.0 Hz, 1H), 6.61 (dd, J=8.5, 3.0, 1H), 3.80 (s, 3H), 3.53 (d, J=16.0 Hz, 1H), 3.10 (d, J=16.0 Hz, 1H), 1.61 (s, 3H).

Intermediate 15

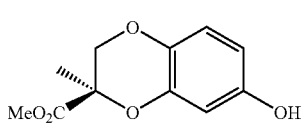

Intermediate 15 was prepared by following the steps described below.

Step 1.
4-methoxy-2-(methoxyethoxy)methoxy-benzaldehyde

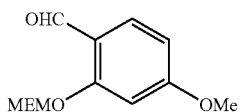

A mixture of 4-methoxy-2-hydroxybenzaldehyde (6.5 g, 40 mmol), MEM-chloride (10.0 g, 80 mmol) and diisopropylethylamine (21 mL, 120 mmol) in dichloromethane (200 mL) was stirred at 25° C. for 14 h. The reaction mixture was concentrated to a small volume, diluted with diethyl ether (200 mL) and filtered through a short path of silica gel. The filtrate was concentrated to give crude 4-methoxy-2-(methoxyethoxy)methoxy-benzaldehyde which was pure enough for use in the next step.

Step 2.
4-methoxy-2-(methoxyethoxy)methoxyphenol

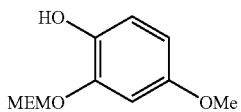

The aldehyde from Step 1 (9.5 g, 40 mmol) was dissolved in dichloromethane (400 mL) followed by the addition of m-chloroperbenzoic acid (70%, ca 80 mmol) and solid sodium bicarbonate (10.1 g, 120 mmol). After being vigorously stirred at 25° C. for 2 h, the reaction mixture was poured into a saturated solution of sodium bicarbonate (400 mL) and stirred for 1 h. The organic layer was separated and the aqueous phase was extracted with dichloromethane. The combined organic phase was washed successively with saturated sodium bisulfite and sodium bicarbonate solution, dried over $Mg_2SO_4$ and concentrated. The residue was purified by chromatography on silica gel to give 7.1 g (78% yield) of the title compound $^1$H NMR (500 MHz, CDCl$_3$) δ 6.88 (d, J=8.5 Hz, 1H), 6.83 (d, J=2.5 Hz, 1H), 6.60 (dd, J=8.5, 2.5 Hz, 1H), 5.0 (s, 2H), 3.88 (m, 2H), 3.61 (m, 2H), 3.80 (s, 3H), 3.42 (s, 3H), Step 3. 2-methyl-7-methoxybenzo[1,4]dioxine-2-ol

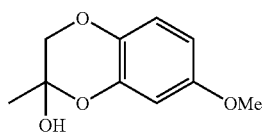

The product from Step 2 (2.28 g, 10 mmol), chloroacetone (4.6 g, 40 mmol) and Cs2CO3 in DMF (100 mL) was vigorously stirred at 25 C for 16 h. The mixture was poured into water (200 mL) and extracted with ethyl acetate (3×80 mL). The combined extracts were washed with water (2×100 mL) and then concentrated. The residued was taken up in THF (100 mL) and treated with 5 N HCl (20 mL) at 45 C for 1 h. The reaction mixture was diluted with brine (100 mL) and extracted with ethyl acetate. The organic phase was washed with brine, dried over MgSO4 and concentrated The residue was purified by chromatography on silica gel eluting with 8:2 ethyl acetate/hexane to afford 1.3 g of the title compound.

Step 4.
2-Methoxy-2-methyl-7-methoxybenzo[1,4]dioxine

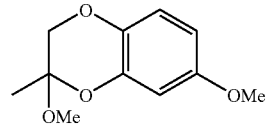

The product from Step 3 was dissolved in anhydrous methanol (50 mL) containing ca. 1% of hydrogen chloride. After being kept at 25 for 6 h, the solution was quenched with triethylamine and concentrated. The residue was diluted with diethyl ether and filtered through a short path of silica gel. Evaporation of the solvent gave the 1.3 g of the title compound.

$^1$H NMR (500 MHz, CDCl$_3$) δ 6.81 (d, J=8.5 Hz, 1H), 6.59 (d, J=2.5 Hz, 1H), 6.36 (dd, J=8.5, 2.5 Hz, 1H), 4.19 (d, J=11.0 Hz, 1H), 3.81 (d, J=11.0 Hz, 1H), 3.80 (s, 3H), 3.35 (s, 3H), 1.60 (s, 3H).

Step 5.
2-Cyano-2-methyl-7-methoxybenzo[1,4]benzodioxine

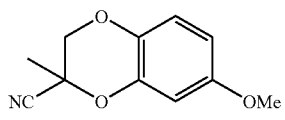

Trifluoroboron etherate (mL, 9.6 mmol) was added to a solution of the product from Step 4 (1.0 g, 4.8 mmol), trimethylsilyl cyanide (2.5 mL, 9.6 mmol) in dichlorormethane (25 mL) cooled in a ice bath. The reaction was kept at 0 C for 1 h and warmed to 25 C over 30 min. Methanol (2.0 mL) was added, followed by addition of water (50 mL). After phase separation and extraction, the crude product was purified by chromatography on silica gel to give 0.73 g (74.8% yield) of the title compound.

$^1$H NMR (500 MHz, CDCl$_3$) δ 6.91 (d, J=8.5 Hz, 1H), 6.56 (dd, J=8.5, 2.5 Hz, 1H), 6.51 (d, J=2.5 Hz, 1H), 4.4 (d, J=11.0 Hz, 1H), 3.9 (d, J=11.0 Hz, 1H), 3.79 (s, 3H), 1.80 (s, 3H).

Step 6. Methyl(±)-2-methyl-7-hydroxybenzo[1,4]dioxine-2-carboxylate

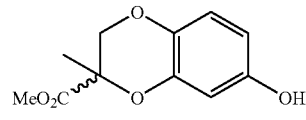

The product from Step 5 (0.6 g, 2.9 mmol) was treated with 2 N KOH in ethanol under reflux for 4 h. Removal of ethanol and acidification of the residue with 2 N HCl gave the crude acid, which was dissolved in dichloromethane (mL) and treated with boron tribromide (1 M in hexane, mL, mmol) at 0 C for 1 h. The reaction was quenched with water and extracted with dichloromethane. The combined extracts were washed with brine and dried over MgSO4. Removal of solvents gave a residue which was taken up in 7:1 benzene/methanol and treated with excess trimethylsilyldiazo methane (1 m in hexane). Removal of solvents and purification of the residue by chromatography on silica gel afforded 0.48 (75% yield) of the title compound as an oil.

Step 7. The racemic product from step 6 was separated on a preparative Chiracel OD column eluting with 10:90 isopropanol/heptane. The late fraction was collected and concentrated to afford intermediate 15 as a white solid.

$^1$H NMR (500 MHz, CDCl$_3$) δ 6.74 (d, J=8.5 Hz, 1H), 6.53(d, J=2.5 Hz, 1H), 6.36 (dd, J=8.5, 2.5 Hz, 1H), 5.08 (br. s, 1H), 4.50 (d, J=11.0 Hz, 1H), 3.90 (d, J=11.0 Hz, 1H), 3.80 (s, 3H), 3.42 (s, 3H), 1.60 (s, 3H).

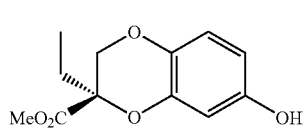

Intermediate 16

Intermediate 16 was prepared following the same synthetic route as described for intermediate 15, using 1-bromo-2-butanone instead of chloroacetone in Step 3.

$^1$H NMR (500 MHz, CDCl$_3$) δ 6.74 (d, J=8.5 Hz, 1H), 6.54 (d, J=2.5 Hz, 1H), 6.36 (dd, J=8.5, 2.5 Hz, 1H), 5.08 (br. s, 1H), 4.51 (d, J=11.0 Hz, 1H), 3.90 (d, J=11.0 Hz, 1H), 3.80 (s, 3H), 3.42 (s, 3H), 2.09 (m, 1H), 1.79 (m, 1H), 1.00 (t, J=7.5 Hz, 3H).

General Procedure 3 for the Preparation of benzo[d]isoxazole-based carboxylic acid Derivatives Step 1. Coupling of the phenol intermediates with 6-fluoro-3-(substituted phenyl)benzo[d]isoxazoles. A mixture of the phenol (0.42 g, 2.0 mmol) and 6-fluoro-3-(substituted phenyl)benzo[d]isoxazole (0.28 g, 1.0 mmol) and Cs$_2$CO$_3$ (0.65 g, 2.0 mmol) in dimethylacetamide (10 mL) are stirred at 100° C. for 6-16 hrs. The reaction is diluted with ethyl acetate and washed with 1 N HCl and water. After removal of solvent, the residue, consisting of the crude coupling product and the corresponding acid, is dissolved in benzene/methanol (7:1, v/v, mL) and treated with (trimethylsilyl)diazomethane (2 M, in hexane) until the gas evolution ceases. The solvent is evaporated and the residue is chromatographed on silica gel to afford the coupling product.

Step 2. Hydrolysis of the coupling product. The product from Step 1 is dissolved in methanol (10 mL) and treated with 2N NaOH (2 mL, 4.0 mmol) at 25-50° C. for 2-6 hrs. The reaction is acidified to pH 2-3 with 2 N HCl and concentrated. The residue is purified by preparative HPLC on a 100×20 mm YMC C-18 column using 10-100% gradient CH$_3$CN—H$_2$O containing 0.1% TFA as the eluent to afford the final carboxylic acid.

EXAMPLE 1

2-Methyl-2-{3-[3-(4-trifluoromethyl-phenyl)-benzo[d]isoxazol-6-yloxy]-phenoxy}-propionic acid

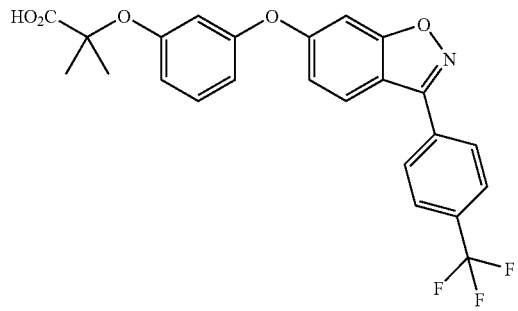

The title compound was prepared following the general procedure 3 using intermediate 8 and intermediate 1 for the coupling reaction.

$^1$H NMR (500 MHz, CD$_3$OD) δ 8.20 (d, J=8.0 Hz, 2H), 8.03 (d, J=9.0 Hz, 1H), 7.92 (d, J=8.0 Hz, 2H), 7.32 (t, J=8.0 Hz, 1H), 7.19 (m, 2H), 6.77 (dd, J=14.0 Hz, 2.5 Hz, 1H), 6.77 (t, J=3.0 Hz, 1H), 6.66 (t, J=3.0 Hz, 1H), 1.58 (s, 6H).

MS (ESI, m/z): 458.0 (M$^+$+1).

EXAMPLE 2

2-Methyl-2-{4-[3-(4-trifluoromethyl-phenyl)-benzo[d]isoxazol-6-yloxy]-phenoxy}-propionic acid

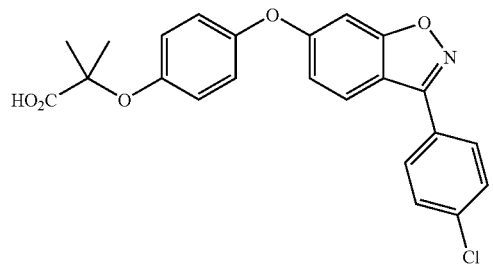

The title compound was prepared following the general procedure 3 using intermediate 12 and intermediate 1 for the coupling reaction.

$^1$H NMR (500 MHz, CDCl$_3$) δ 8.16 (d, J=7.0 Hz, 2H), 7.97 (d, J=7.0 Hz, 1H), 7.89 (d, J=7.0 Hz, 2H), 7.13 (dd, J=7.0, 1.5 Hz, 1H), 7.07 (d, J=1.5 Hz, 1H), 7.04 (d, J=7.0, 2H), 6.99 (d, J=7.0, 2H), 1.59 (s, 6H).

MS (ESI, m/z): 458.4 (M$^+$+1).

EXAMPLE 3

2-Methyl-2-{3-[3-(4-trifluoromethoxy-phenyl)-benzo[d]isoxazol-6-yloxy]-phenoxy}-propionic acid

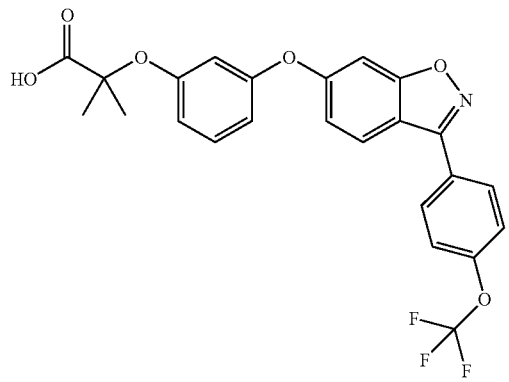

The title compound was prepared following the general procedure 3 using intermediate 8 and intermediate 2 for the coupling reaction.

$^1$H NMR (500 MHz, CD$_3$OD) δ 8.11 (d, J=8.5 Hz, 2H), 7.97 (d, J=9.5 Hz, 1H), 7.52 (d, J=8.0 Hz, 2H), 7.26 (t, J=8.5 Hz, 1H), 7.15 (m,2H), 6.80 (dd, J=8.0 Hz, 2.5 Hz, 1H), 6.71 (t, J=3.0 Hz, 1H), 6.64 (dd, J=8.0 Hz, 2.5 Hz, 1H), 1.54 (s, 6H).

MS (ESI, m/z): 474.3 (M$^+$+1).

EXAMPLE 4

2-Methyl-2-{3-[3-(4-chloro-phenyl)-benzo[d]isoxazol-6-yloxy]-phenoxy}-propionic acid

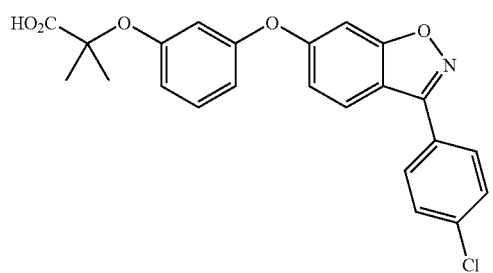

The title compound was prepared following the general procedure 3 using intermediate 8 and intermediate 3 for the coupling reaction.

$^1$H NMR (500 MHz, CDCl$_3$) δ 7.95 (d, J=8.5 Hz, 2H), 7.60 (m, 3H), 7.30 (t, J=7.8 Hz, 1H), 7.14 (d, J=1.8 Hz, 1H), 7.12 (dd, J=9.0, 1.8 Hz, 1H), 6.74 (m, 2H), 6.63 (t, J=2.0, 1H), 1.57 (s, 6H).

MS (ESI, m/z): 424.3 (M$^+$+1)

EXAMPLE 5

2-Methyl-2-{3-[3-(4-isopropy-phenyl)-benzo[d]isoxazol-6-yloxy]-phenoxy}-propionic acid

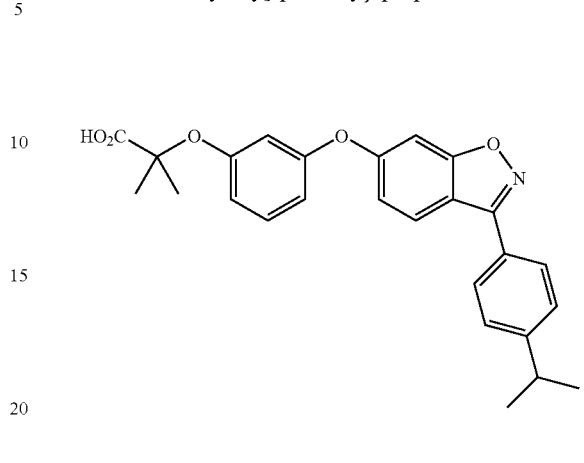

The title compound was prepared following the general procedure 3, using intermediate 8 and intermediate 5 for the coupling reaction.

$^1$H NMR (500 MHz, CD$_3$OD) δ 7.95 (d, J=8.7 Hz, 1H), 7.87 (d, J=8.1 Hz, 2H), 7.45 (d, J=8.1 Hz, 2H), 7.29 (t, J=8.2 Hz, 1H), 7.12 (m, 2H), 6.74 (m, 2H), 6.63 (t, J=2.3 Hz, 1H), 3.52 (d, J=16.9 Hz, 1H), 3.00 (m, 1H), 1.58 (s, 6H), 1.30 (d, J=7.0 Hz, 6H).

MS (ESI, m/z): 432.4 (M$^+$+1).

EXAMPLE 6

2-Methyl-2-{3-[3-(4-ethyl-phenyl)-benzo[d]isoxazol-6-yloxy]-phenoxy}-propionic acid

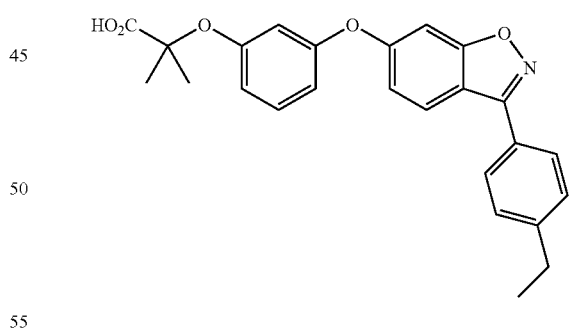

The title compound was prepared following the general procedure 3 using intermediate 8 and intermediate 4 for the coupling reaction.

$^1$H NMR (600 MHz, CD$_3$OD) δ 7.96 (d, J=8.4 Hz, 1H), 7.86 (d, J=8.4 Hz, 2H), 7.42 (d, J=7.8 Hz, 2H), 7.30 (t, J=8.4 Hz, 1H), 7.13 (d, J=1.8 Hz, 1H), 7.11 (dd, J=8.4 Hz, 1.8 Hz, 1H), 6.74 (m, 2H), 6.63 (t, J=2.4 Hz, 1H), 2.74 (q, J=7.8 Hz, 2H), 1.57 (s, 6H), 1.28 (t, J=7.8 Hz, 3H).

MS (ESI, m/z): 418.3 (M$^+$+1).

EXAMPLE 7

2-Methyl-2-{3-[3-(3-trifluoromethyl-phenyl)-benzo[d]isoxazol-6-yloxy]-phenoxy}-propionic acid

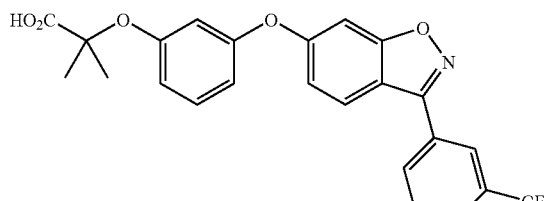

The title compound was prepared following the general procedure 3 using intermediate 8 and intermediate 6 for the coupling reaction.

$^1$H NMR (500 MHz, CD$_3$OD) δ 8.24 (m, 2H), 7.97 (d, J=9.4 Hz, 1H), 7.89 (br d, J=7.8 Hz, 1H), 7.82 (t, J=7.8 Hz, 1H), 7.32 (t, J=8.2 Hz, 1H), 7.17 (m, 2H), 6.76 (m, 2H), 6.66 (br m, 1H), 1.58 (s, 6H).

MS (ESI, m/z): 458.0 (M$^+$+1).

EXAMPLE 8

2-{3-[3-(4-trifluoromethyl-phenyl)-benzo[d]isoxazol-6-yloxy]-phenoxy}-propionic acid

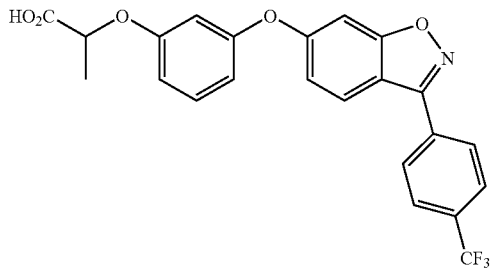

The title compound was prepared following the general procedure 3 using intermediate 9 and intermediate 1 for the coupling reaction.

$^1$H NMR (500 MHz, CD$_3$OD) δ 8.19 (d, J=8.3 Hz, 2H), 8.02 (d, J=8.4 Hz, 1H), 7.91 (d, J=8.2 Hz, 2H), 7.34 (t, J=8.2 Hz, 1H), 7.19 (m, 2H), 6.79 (dd, J=8.2, 2.1 Hz, 1H), 6.73 (dd, J=8.2, 2.1 Hz, 1H), 6.73 (dd, J=8.2, 2.1 Hz, 1H), 6.68 (m, 1H), 4.81 (m, 1H), 1.59 (d, J=6.7 Hz, 3H).

MS (ESI, m/z): 444.3 (M$^+$+1).

EXAMPLE 9

2-{3-[3-(4-chloro-phenyl)-benzo[d]isoxazol-6-yloxy]-phenoxy}-butanoic acid

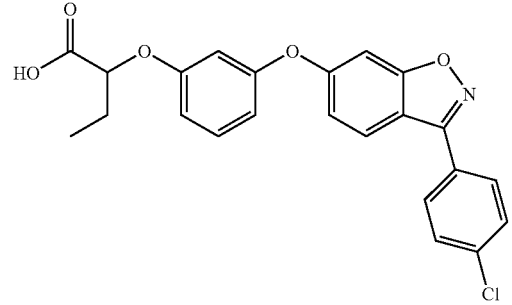

The title compound was prepared following the general procedure 3 using intermediate 10 and intermediate 3 for the coupling reaction.

$^1$H NMR (500 MHz, CDCl$_3$) δ 7.91 (d, J=8.5 Hz, 2H), 7.82 (d, J=8.5 Hz, 1H), 7.57 (d, J=9.0 Hz, 2H), 7.34 (t, J=8.0 Hz, 1H), 7.17 (d, J=1.5 Hz, 1H), 7.14 (dd, J=8.0 Hz, 1.5 Hz, 1H), 6.77 (m, 2H), 6.71 (t, J=2.0 Hz, 1H), 4.66 (t, J=6.0 Hz, 1H), 2.07 (m, 2H), 1.13 (t, J=7.5 Hz, 3H).

MS (ESI, m/z): 424.3 (M$^+$+1).

EXAMPLE 10

2-{3-[3-(4-trifluoromethyl-phenyl)-benzo[d]isoxazol-6-yloxy]-phenoxy}-butanoic acid

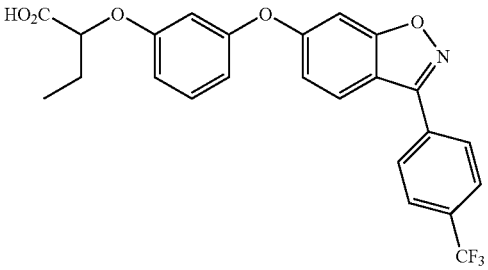

The title compound was prepared following the general procedure 3, using intermediate 10 and intermediate 1 for the coupling reaction.

$^1$H NMR (500 MHz, CD$_3$OD) δ 8.19 (d, J=8.0 Hz, 2H), 8.02 (d, J=8.6 Hz, 1H), 7.91 (d, J=8.2 Hz, 2H), 7.35 (t, J=8.2 Hz, 1H), 7.19 (m, 2H), 6.79 (dd, J=8.2, 2.2 Hz, 1H), 6.73 (dd, J=8.2, 1.9 Hz, 1H), 6.73 (dd, J=8.2, 1.9 Hz, 1H), 6.68 (t, J=2.3 Hz, 1H), 4.66 (m, 1H), 1.98 (m, 2H), 1.08 (t, J=7.3 Hz, 3H).

MS (ESI, m/z): 458.4 (M$^+$+1).

EXAMPLE 11

3-Methyl-2-{3-[3-(4-trifluoromethyl-phenyl)-benzo[d]isoxazol-6-yloxy]-phenoxy}-butanoic acid

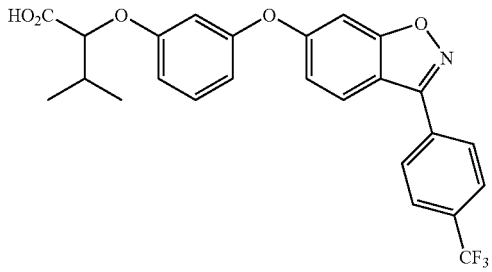

The title compound was prepared following the general procedure 3 using intermediate 11 and intermediate 1 for the coupling reaction.

$^1$H NMR (500 MHz, CD$_3$OD) δ 8.20 (d, J=8.2 Hz, 2H), 8.03 (d, J=8.7 Hz, 1H), 7.92 (d, J=8.2 Hz, 2H), 7.35 (t, J=8.2 Hz, 1H), 7.19 (m, 2H), 6.80 (dd, J=8.3, 2.2 Hz, 1H), 6.73 (dd, J=8.0, 2.0 Hz, 1H), 6.68 (t, J=2.3 Hz, 1H), 4.47 (d, J=4.8 Hz, 1H), 2.28 (m, 1H), 1.09 (d, J=6.9 Hz, 6H).

MS (ESI, m/z): 472.4 (M$^+$+1).

EXAMPLE 12

2-{2-fluoro-3-[3-(4-trifluoromethyl-phenyl)-benzo[d]isoxazol-6-yloxy]-phenoxy}-butanoic acid

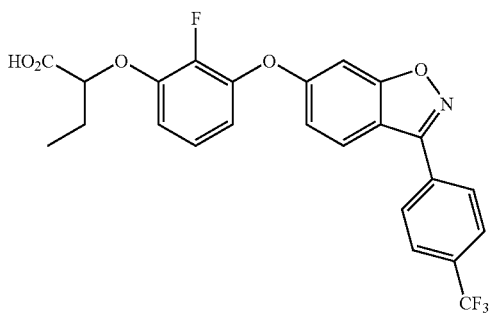

A solution of the title compound of example 10 (92 mg, 0.2 mmol) and SELECTFLUOR™ (Aldrich, 70 mg, 0.2 mmol) in acetonitrile (2.0 mL) was heated at 60° C. for 16 hrs. The reaction mixture was directly purified by preparative HPLC on a 100×20 mm YMC C-18 column using 0.1% TFA modified CH$_3$CN—H$_2$O solvent system as the eluent to afford the title compound.

$^1$H NMR (500 MHz, CD$_3$OD) δ 8.17 (d, J=8.1 Hz, 2H), 8.00 (d, J=9.3 Hz, 1H), 7.89 (d, J=8.1 Hz, 2H), 7.17 (m, 3H), 6.77 (m, 1H), 6.70 (m, 1H), 4.63 (m, 1H), 1.99 (m, 2H), 1.08 (t, J=7.4 Hz, 3H).

MS (ESI, m/z): 476.3 (M$^+$+1).

EXAMPLE 13

2-{3-[3-(4-Dimethylamino-phenyl)-benzo[d]isoxazol-6-yloxy]-phenoxy}-2-methyl-propionic acid

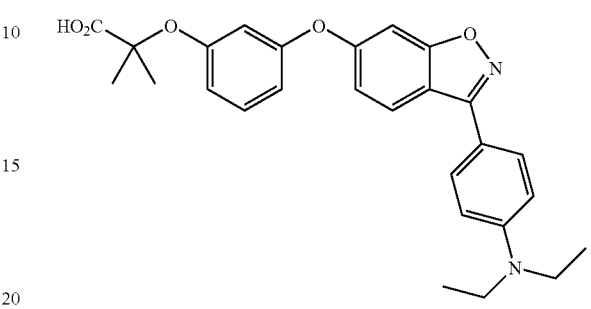

The title compound was prepared following the general procedure 3 using intermediate 8 and intermediate 7 for the coupling reaction.

$^1$H NMR (500 MHz, CDCl$_3$) δ 8.14 (d, J=9.0 Hz, 2H), 7.84 (d, J=9.5 Hz, 1H), 7.77 (d, J=8.5 Hz, 2H), 7.34 (t, J=8.5 Hz, 1H), 7.17 (m, 2H), 6.84 (m, 2H), 6.74 (t, J=2.5 Hz, 1H), 3.63 (q, J=7.0 Hz, 2H), 1.67 (s, 6H), 1.28 (t, J=7.0 Hz, 3H).

MS (ESI, m/z): 461.1 (M$^+$+1).

EXAMPLE 14

(2S)-2-Ethyl-5-[3-(4-trifluoromethyl-phenyl)-benzo[d]isoxazol-6-yloxy]-2,3-dihydro-benzofuran-2-carboxylic acid

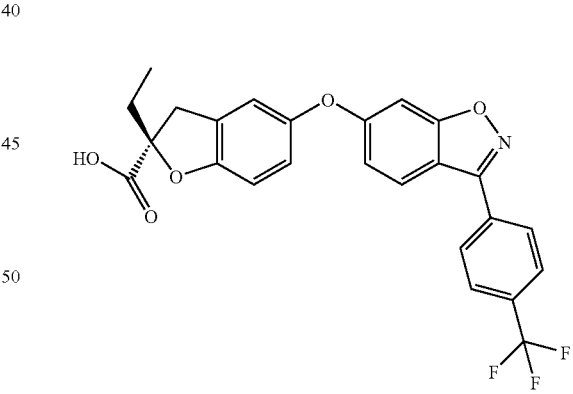

The title compound was prepared following the general procedure 3 using intermediate 13 and intermediate 1 for the coupling reaction.

$^1$H NMR (600 MHz, CD$_3$OD) δ 8.16 (d, J=7.8 Hz, 2H), 7.96 (dd, J=9.0 Hz, 3.0 Hz, 1H), 7.89 (d, J=7.8 Hz, 2H), 7.13 (d, J=9.0 Hz, 1H), 7.05 (s, 1H), 7.00 (s, 1H), 6.92 (d, J=9.0 Hz, 1H), 6.86 (d, J=9.0 Hz, 1H), 3.56 (d, J=16.8 Hz, 1H), 3.26 (d, J=16.2 Hz, 1H), 2.09 (m, 1H), 2.00 (m, 1H), 1.03 (t, J=7.2 Hz, 3H).

MS (ESI, m/z): 470.3 (M$^+$+1).

EXAMPLE 15

(2R)-2-Isopropyl-5-[3-(4-trifluoromethyl-phenyl)-benzo[d]isoxazol-6-yloxy]-2,3-dihydro-benzofuran-2-carboxylic acid

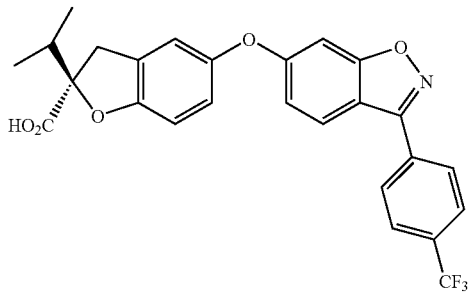

The title compound was prepared following the general procedure 3 using intermediate 14 and intermediate 1 for the coupling reaction.

$^1$H NMR (500 MHz, CDCl$_3$) δ 8.16 (d, J=7.0 Hz, 2H), 7.96 (d, J=7.5 Hz, 1H), 7.88 (d, J=7.0 Hz, 2H), 7.13 (dd, J=7.5, 1.5 Hz, 1H), 7.04 (d, J=1.5 Hz, 1H), 6.98 (d, J=1.0 Hz, 1H), 6.89 (dd, J=7.0, 1.0 Hz, 1H), 6.85 (d, J=7.0 Hz, 1H), 3.53 (d, J=11.4 Hz, 1H), 3.35 (d, J=11.4 Hz, 1H), 2.32 (m, 1H), 1.06 (d, J=6.6 Hz, 3H), 0.99 (d, J=6.6 Hz, 3H).

MS (ESI, m/z): 484.5 (M$^+$+1).

EXAMPLE 16

(2R)-2-Isopropyl-5-[3-(4-isopropyl-phenyl)-benzo[d]isoxazol-6-yloxy]-2,3-dihydro-benzofuran-2-carboxylic acid

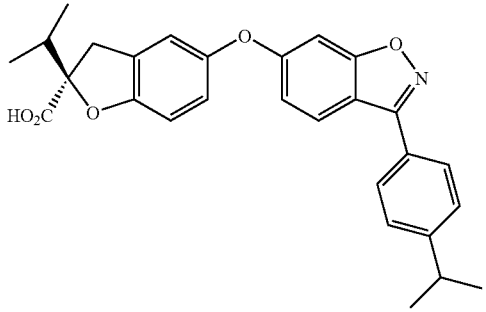

The title compound was prepared following the general procedure 3 using intermediate 14 and intermediate 5 for the coupling reaction.

$^1$H NMR (500 MHz, CD$_3$OD) δ 7.90 (d, J=8.8 Hz, 1H), 7.85 (d, J=8.1 Hz, 2H), 7.44 (d, J=6.2 Hz, 2H), 7.08 (dd, J=8.8, 2.1 Hz, 1H), 7.00 (d, J=1.9 Hz, 1H), 6.98 (d, J=2.3 Hz, 1H), 6.89 (m, 1H), 6.85 (m, 1H), 3.52 (d, J=16.9 Hz, 1H), 3.36 (d, J=16.9 Hz, 1H), 2.99 (m, 1H), 2.32 (m, 1H), 1.29 (d, J=7.0 Hz, 6H), 1.05 (d, J=6.8 Hz, 3H) 0.99 (d, J=6.8 Hz, 3H).

MS (ESI, m/z): 458.4 (M$^+$+1).

EXAMPLE 17

(2R)-2-Isopropyl-5-[3-(4-chloro-phenyl)-benzo[d]isoxazol-6-yloxy]-2,3-dihydro-benzofuran-2-carboxylic acid

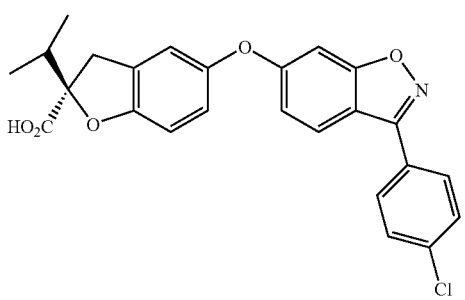

The title compound was prepared following the general procedure 3 using intermediate 14 and intermediate 3 for the coupling reaction.

$^1$H NMR (500 MHz, CDCl$_3$) δ 7.95 (d, J=7.0 Hz, 2H), 7.92 (d, J=7.5 Hz, 1H), 7.59 (d, J=7.0 Hz, 2H), 7.10 (dd, J=7.5, 1.5 Hz, 1H), 7.02 (d, J=1.5 Hz, 1H), 6.98 (d, J=1.0 Hz, 1H), 6.90 (dd, J=7.5, 1.5 Hz, 1H), 6.85 (d, J=7.5 Hz, 1H), 3.53 (d, J=11.4 Hz, 1H), 3.36 (d, J=11.4 Hz, 1H), 2.32 (m, 1H), 1.06 (d, J=6.6 Hz, 3H), 0.99 (d, J=6.6 Hz, 3H).

MS (ESI, m/z): 450.3 (M$^+$+1).

EXAMPLE 18

(2R)-2-Isopropyl-5-[3-(4-trifluoromethoxy-phenyl)-benzo[d]isoxazol-6-yloxy]-2,3-dihydro-benzofuran-2-carboxylic acid

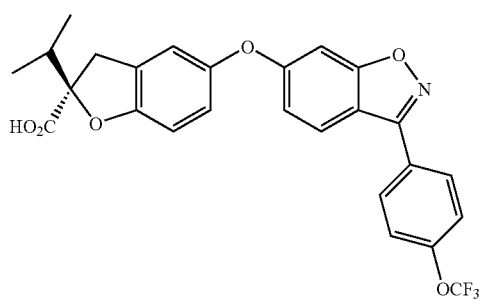

The title compound was prepared following the general procedure 3 using intermediate 14 and intermediate 2 for the coupling reaction.

$^1$H NMR (500 MHz, CDCl$_3$) δ 8.06 (d, J=7.0 Hz, 2H), 7.95 (d, J=7.5 Hz, 1H), 7.46 (d, J=7.0 Hz, 2H), 7.13 (dd, J=7.5, 1.5 Hz, 1H), 7.04 (d, J=1.5 Hz, 1H), 6.98 (d, J=1.0 Hz, 1H), 6.89 (dd, J=7.0, 1.0 Hz, 1H), 6.85 (d, J=7.0 Hz, 1H), 3.53 (d, J=11.4 Hz, 1H), 3.35 (d, J=11.4 Hz, 1H), 2.32 (m, 1H), 1.06 (d, J=6.6 Hz, 3H), 0.99 (d, J=6.6 Hz, 3H).

MS (ESI, m/z): 500.5 (M$^+$+1).

EXAMPLE 19

(2R)-2-Methyl-7-[3-(4-trifluoromethyl-phenyl)-benzo[d]isoxazol-6-yloxy]-2,3-dihydro-benzo[1,4]dioxine-2-carboxylic acid

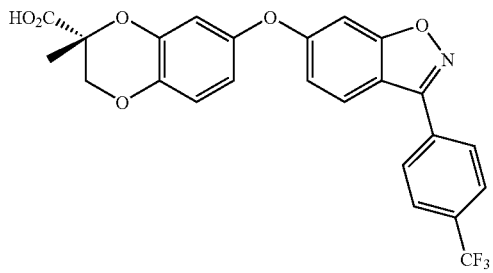

The title compound was prepared following the general procedure 3 using intermediate 15 and intermediate 1 for the coupling reaction.

$^1$H NMR (500 MHz, CDCl$_3$) δ 8.17 (d, J=7.0 Hz, 2H), 7.98 (d, J=7.5 Hz, 1H), 7.89 (d, J=7.0 Hz, 2H), 7.15 (dd, J=7.5, 1.5 Hz, 1H), 7.11 (d, J=1.5 Hz, 1H), 6.91 (d, J=7.0 Hz, 1H), 6.73 (d, J=2.0 Hz, 1H), 6.63 (dd, J=7.0, 2.0 Hz, 1H), 4.57 (d, J=11.4 Hz, 1H), 3.92 (d, J=11.4 Hz, 1H), 1.55 (s, 3H).

MS (ESI, m/z): 472.0 (M$^+$+1).

EXAMPLE 20

(2R)-2-Ethyl-7-[3-(4-trifluoromethyl-phenyl)-benzo[d]isoxazol-6-yloxy]-2,3-dihydro-benzo[1,4]dioxine-2-carboxylic acid

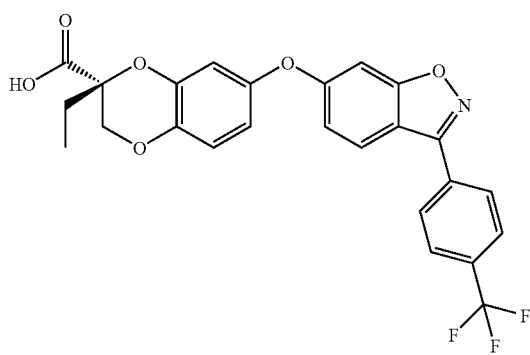

The title compound was prepared following the general procedure 3 using intermediate 16 and intermediate 1 for the coupling reaction.

$^1$H NMR (600 MHz, CD$_3$OD) δ 8.19 (d, J=8.0 Hz, 2H), 8.00 (d, J=9.0 Hz, 1H), 7.91 (d, J=8.0 Hz, 2H), 7.18 (dd, J=9.0 Hz, 2.0 Hz, 1H), 7.14 (d, J=2 Hz, 1H), 6.92 (d, J=9.0 Hz, 1H), 6.77 (d, J=3.0 Hz, 1H), 6.64 (dd, J=9.0 Hz, 3.0 Hz, 1H), 4.56 (d, J=11.5 Hz, 1H), 3.97 (d, J=11.0 Hz, 1H), 1.99 (m, 1H), 1.87 (m, 1H), 1.07 (t, J=7.5 Hz, 3H).

MS (ESI, m/z): 486.0 (M$^+$+1).

EXAMPLE 21

(2R)-2-Ethyl-7-[3-(4-trifluoromethoxy-phenyl)-benzo[d]isoxazol-6-yloxy]-2,3-dihydro-benzo[1,4]dioxine-2-carboxylic acid

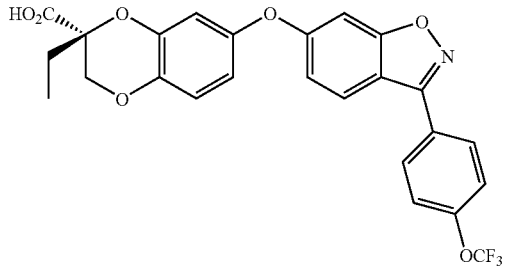

The title compound was prepared following the general procedure 3 using intermediate 16 and intermediate 2 for the coupling reaction.

$^1$H NMR (500 MHz, CD$_3$OD) δ 8.08 (m, 2H), 7.95 (d, J=8.7 Hz, 1H), 7.49 (d, J=8.3 Hz, 2H), 7.14 (m, 1H), 7.10 (d, J=2.0Hz, 1H), 6.88 (d, J=8.6 Hz, 1H), 6.75 (d, J=2.5 Hz, 1H), 6.59 (dd, J=8.6, 2.6 Hz, 1H), 4.52 (d, J=11.1 Hz, 1H), 3.95 (d, J=11.1 Hz, 1H), 1.96 (m, 1H), 1.83 (m, 1H), 1.04 (t, J=7.2 Hz, 3H).

MS (ESI, m/z): 502.2 (M$^+$+1).

EXAMPLE 22

A tablet formulation for a direct compression process that yields a 50 mg dose of a compound of Formula I as the active pharmaceutical ingredient (API) is made as follows. The tablet comprises 50 mg of the compound, 65 mg of microcrystalline cellulose, 65 mg of mannitol (or 65 mg of dicalcium phosphate), 4 mg of croscarmellose sodium, 4 mg of magnesium stearate and 8 mg of Opadry White (a proprietary coating material made by Colorcon, West Point, Pa.). The API, microcrystalline cellulose, mannitol (or dicalcium phosphate), and croscarmellose sodium are first blended, and the mixture is then lubricated with magnesium stearate and pressed into tablets. The tablets are then film coated with Opadry White.

The foregoing examples are provided so that the invention will be more fully appreciated and understood. The examples should not be construed as limiting the invention in any way. The scope of the invention is defined by the appended claims.

What is claimed is:

1. A compound having Formula I, or a pharmaceutically acceptable salt thereof, wherein

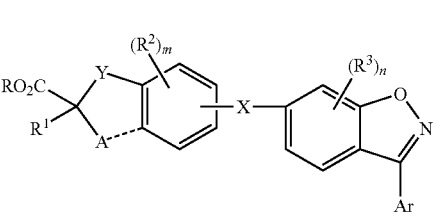

I

X and Y are independently selected from O and S;

A is selected from the group consisting of H, —C$_1$-C$_3$ alkyl which is optionally substituted with 1-5 halogens, —CR$^4$R$^5$—, and —CR$^4$R$^5$O—, wherein when A is —CR$^4$R$^5$— or —CR$^4$R$^5$O—, the dotted line between A and the phenyl ring of Formula I represents a single bond, and when A is —CR$^4$R$^5$O—, the O of —CR⁴R⁵O— is connected to the phenyl ring, and when A is H or —$C_1$-$C_3$ alkyl, the dotted line does not represent a bond;

R is selected from the group consisting of H and $C_{1-6}$ alkyl, which is optionally substituted with 1-5 halogens;

$R^1$ is selected from the group consistently of H, halogen, and $C_1$-$C_4$ alkyl, which is optionally substituted with 1-5 halogens;

$R^2$ and $R^3$ are independently selected from the group consisting of halogen, $C_2$-$C_4$alkenyl, and $C_1$-$C_4$alkyl, wherein $C_1$-$C_4$alkyl and C2-C4alkenyl are optionally substituted with 1-5 halogens;

$R^4$ and $R^5$ are independently selected from the group consisting of H, halogen, and $C_1$-$C_3$ alkyl, wherein $C_1$-$C_3$ alkyl is optionally substituted with 1-5 halogens;

m is 0, 1, or 2;

n is 0, 1, or 2;

Ar is phenyl, which is optionally substituted with 1-3 substituent groups independently selected from halogen —$C_1$-$C_4$alkyl, —$OC_1$-$C_4$alkyl, and —$NR^6R^7$, wherein —$C_1$-$C_4$alkyl and —$OC_1$-$C_4$alkyl are optionally substituted with 1-5 halogens; and $R^6$ and $R^7$ are each independently selected from H and $C_1$-$C_3$alkyl.

2. The compound of claim 1, or a pharmaceutically acceptable salt thereof, wherein X and Y are O and are meta or para to each other;

$R^1$ is selected from —$CH_3$, —$C_2H_5$, n-$C_3H_7$, and —CH($CH_3$)$_2$;

$R^2$ and $R^3$ are independently selected from halogen, —$C_1$-$C_3$alkyl, and —$C_2$-$C_3$alkenyl, wherein —$C_1$-$C_3$ alkyl and —$C_2$-$C_3$alkenyl are optionally substituted with 1-3 halogens;

m and n are each independently 0 or 1;

A is selected from the group consisting of H, —$CH_3$, —$CH_2$— and —$CH_2O$—, wherein when A is H or —$CH_3$, the dotted line does not represent a bond; and when A is —$CH_2$— or —$CH_2O$—, the dotted line between A and the phenyl ring of Figure I represents a single bond, and the O of —$CH_2O$— is connected to the phenyl ring;

Ar is phenyl which is optionally substituted with 1-2 groups which are independently selected from —$CF_3$, —$OCF_3$, $C_1$-$C_3$ alkyl, halogen, and —$NR^6R^7$; and $R^6$ and $R^7$ are independently selected from H and $C_1$-$C_3$ alkyl.

3. The compound of claim 1, having Formula Ia, or a pharmaceutically acceptable salt thereof:

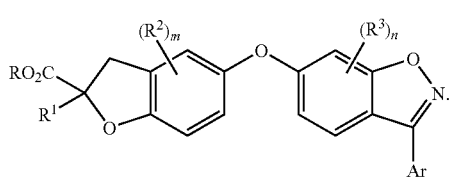

4. The compound of claim 3, or a pharmaceutically acceptable salt thereof, wherein $R^1$ is selected from the group consisting of —$CH_3$, —$C_2H_5$, n-$C_3H_7$, and —CH($CH_3$)$_2$;

$R^2$ and $R^3$ are independently selected from the group consisting of halogen, —$C_1$-$C_3$alkyl, and —$C_2$-$C_3$alkenyl, wherein —$C_1$-$C_3$alkyl, and —$C_2$-$C_3$alkenyl are optionally substituted with 1-3 halogens;

m and n are each independently 0 or 1;

Ar is phenyl which is optionally substituted with 1-2 groups which are independently selected from —$CF_3$, —$OCF_3$, —$C_1$-$C_3$ alkyl, halogen, and $NR^6R^7$; and $R^6$ and $R^7$ are independently selected from the group consisting of H and —$C_1$-$C_3$ alkyl.

5. The compound of claim 1, having Formula Ib, or a pharmaceutically acceptable salt thereof:

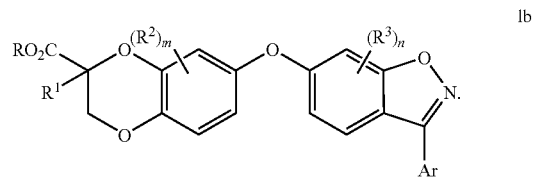

6. The compound of claim 5, or a pharmaceutically acceptable salt thereof, wherein $R^1$ is selected from the group consisting of —$CH_3$, —$C_2H_5$, n-$C_3H_7$, and —CH($CH_3$)$_2$;

$R^2$ and $R^3$ are each independently selected from the group consisting of halogen, —$C_1$-$C_3$alkyl, and —$C_2$-$C_3$alkenyl, wherein —$C_1$-$C_3$alkyl, and —$C_2$-$C_3$alkenyl are optionally substituted with 1-3 halogens;

m and n are each independently 0 or 1;

Ar is phenyl which is optionally substituted with 1-2 groups which are independently selected from —$CF_3$, —$OCF_3$, —$C_1$-$C_3$ alkyl, halogen, and $NR^6R^7$; and $R^6$ and $R^7$ are independently selected from the group consisting of H and —$C_1$-$C_3$ alkyl.

7. The compound of claim 1, having Formula Ic, or a pharmaceutically acceptable salt thereof:

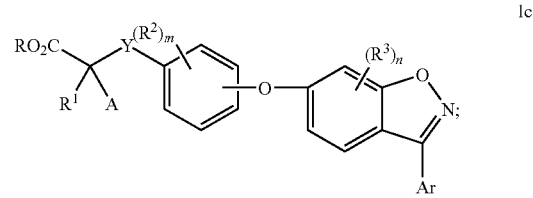

wherein Y is O and is meta or para to the O substituent on the phenyl ring to which Y is attached; and A is selected from the group consisting of H and —$C_1$-$C_3$ alkyl, which is optionally substituted with 1-5 halogens.

8. The compound of claim 7, or a pharmaceutically acceptable salt thereof, wherein $R^1$ is selected from the group consisting of —$CH_3$, —$C_2H_5$, n-$C_3H_7$, and —CH($CH_3$)$_2$;

A is selected from the group consisting of H and —$CH_3$;

$R^2$ and $R^3$ are independently selected from the group consisting of halogen, —$C_1$-$C_3$alkyl, and —$C_2$-$C_3$alkenyl, wherein —$C_1$-$C_3$alkyl, and —$C_2$-$C_3$alkenyl are optionally substituted with 1-3 halogens;

m and n are each independently 0 or 1;

Ar is phenyl which is optionally substituted with 1-2 groups which are independently selected from —$CF_3$, —$OCF_3$, —$C_1$-$C_3$ alkyl, halogen, and $NR^6R^7$; and $R^6$ and $R^7$ are independently selected from the group consisting of H and —$C_1$-$C_3$ alkyl.

9. The compound of claim 1 selected from the group consisting of the compounds below, or a pharmaceutically acceptable salt thereof:

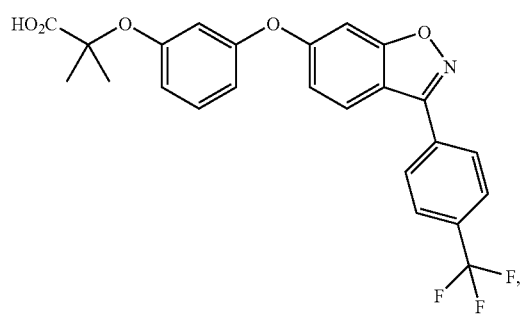
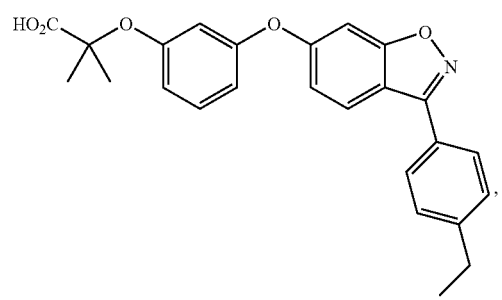

-continued

-continued

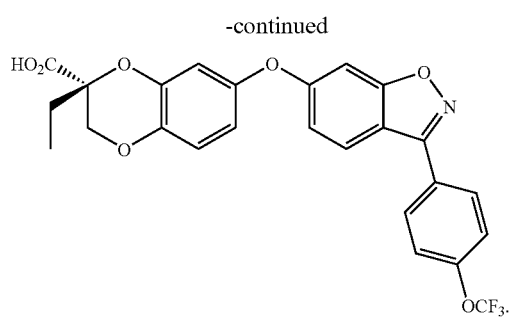

(21)

10. A pharmaceutical composition comprising the compound of claim 1, or a pharmaceutically acceptable salt thereof, and a pharmaceutically acceptable carrier.

11. A method for treating dyslidemia in a patient in need of such treatment which comprises administering to said patient a therapeutically effective amount of the compound of claim 1, or a pharmaceutically acceptable salt thereof.

12. A method for treating atherosclerosis in a patient in need of such treatment which comprises administering to said patient a therapeutically effective amount of the compound of claim 1, or a pharmaceutically acceptable salt thereof.

\* \* \* \* \*